United States Patent
Leiber

(10) Patent No.: US 6,927,304 B2
(45) Date of Patent: Aug. 9, 2005

(54) DE-OXYGENATION TREATMENT FOR NOBLE METAL ON CARBON CATALYSTS USED IN LIQUID PHASE OXIDATION REACTIONS

(75) Inventor: Mark A. Leiber, St. Peters, MO (US)

(73) Assignee: Monsanto Technology LLC, St. Louis, MO (US)

(*) Notice: Subject to any disclaimer, the term of this patent is extended or adjusted under 35 U.S.C. 154(b) by 273 days.

(21) Appl. No.: 10/295,765

(22) Filed: Nov. 15, 2002

(65) Prior Publication Data
US 2003/0171611 A1 Sep. 11, 2003

Related U.S. Application Data

(63) Continuation-in-part of application No. 09/863,885, filed on May 22, 2001.
(60) Provisional application No. 60/206,562, filed on May 22, 2000, provisional application No. 60/220,140, filed on Jul. 21, 2000, and provisional application No. 60/230,240, filed on Sep. 1, 2000.

(51) Int. Cl.$^7$ .................................................. C07F 9/28
(52) U.S. Cl. ...................................................... 562/17
(58) Field of Search .......................................... 562/17

(56) References Cited

U.S. PATENT DOCUMENTS

| 3,950,402 A | 4/1976 | Franz |
| 3,969,398 A | 7/1976 | Hershman |
| 4,582,650 A | 4/1986 | Felthouse |
| 4,624,937 A | 11/1986 | Chou |
| 4,696,772 A | 9/1987 | Chou |
| 5,179,228 A | 1/1993 | Ramon et al. |
| 5,606,107 A | 2/1997 | Smith |
| 6,005,140 A | 12/1999 | Morgenstern et al. |
| 6,232,494 B1 | 5/2001 | Morgenstern et al. |
| 6,239,312 B1 | 5/2001 | Villanti et al. |
| 6,417,133 B1 | 7/2002 | Ebner et al. |
| 2002/0016503 A1 | 2/2002 | Leiber et al. |
| 2002/0068836 A1 | 6/2002 | Haupfear et al. |

FOREIGN PATENT DOCUMENTS

WO    WO 99/52630    10/1999

OTHER PUBLICATIONS

Franz et al., "Glyphosate: A Unique Global Herbicide", ACS Monograph 189, 1997, pp. 233–263, American Chemical Society, Washington D.C.

*Primary Examiner*—Paul A. Zucker
(74) *Attorney, Agent, or Firm*—Senniger Powers; Joseph A. Schaper

(57) ABSTRACT

A treatment for de-oxygenating a noble metal on carbon catalyst used in liquid phase oxidation reactions which includes exposing the catalyst to a non-oxidizing environment. The de-oxygenation treatment improves catalyst performance and is particularly suited for noble metal on carbon catalysts used to catalyze the oxidative cleavage of a carboxymethyl substituent from an N-(phosphonomethyl) iminodiacetic acid substrate in an aqueous reaction mixture using an oxygen-containing gas to produce an N-(phosphonomethyl)glycine product. In one embodiment, the catalyst is exposed to a non-oxidizing environment by introducing a non-oxidizing gas and/or reducing gas into a slurry comprising the catalyst in contact with a liquid medium.

51 Claims, 1 Drawing Sheet

DE-OXYGENATION TREATMENT FOR NOBLE METAL ON CARBON CATALYSTS USED IN LIQUID PHASE OXIDATION REACTIONS

This application is a continuation-in-part of U.S. Ser. No. 09/863,885, filed May 22, 2001, which claims the benefit of U.S. provisional application Ser. No. 60/206,562, filed May 22, 2000, U.S. provisional application Ser. No. 60/220,140, filed Jul. 21, 2000, and U.S. provisional application Ser. No. 60/230,240, filed Sep. 1, 2000, the entire disclosures of which are incorporated herein by reference.

FIELD OF THE INVENTION

The present invention relates generally to processes for liquid phase oxidation of a reagent in an aqueous reaction mixture comprising contacting the aqueous reaction mixture containing the reagent with an oxygen-containing gas in the presence of a heterogenous oxidation catalyst comprising a noble metal deposited on a carbon support. For example, the processes disclosed may be used in the preparation of N-(phosphonomethyl)glycine (also known in the agricultural chemical industry as glyphosate) and related compounds. More particularly, this invention relates to liquid phase oxidation processes wherein an N-(phosphonomethyl)iminodiacetic acid substrate or an N-substituted-N-(phosphonomethyl)glycine substrate (e.g., N-methyl-N-(phosphonomethyl)glycine) is contacted with an oxygen-containing gas in the presence of a heterogenous oxidation catalyst comprising a noble metal deposited on a carbon support to produce an N-(phosphonomethyl)glycine product and the catalyst is recovered and recycled for use again in catalyzing the oxidation reaction.

BACKGROUND OF THE INVENTION

N-(phosphonomethyl)glycine and its salts are conveniently applied as a post-emergent herbicide in aqueous formulations. It is a highly effective and commercially important broad-spectrum herbicide useful in killing or controlling the growth of a wide variety of plants, including germinating seeds, emerging seedlings, maturing and established woody and herbaceous vegetation, and aquatic plants.

One of the more widely accepted methods of making N-(phosphonomethyl)glycine compounds comprises liquid phase oxidative cleavage of a carboxymethyl substituent from an N-(phosphonomethyl)iminodiacetic acid substrate using an oxygen-containing gas in the presence of a heterogenous oxidation catalyst. For example, N-(phosphonomethyl)glycine may be prepared by the liquid phase oxidative cleavage of N-(phosphonomethyl)iminodiacetic acid with oxygen in accordance with the following reaction:

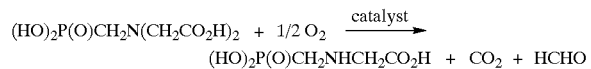

$(HO)_2P(O)CH_2N(CH_2CO_2H)_2 + 1/2\ O_2 \xrightarrow{\text{catalyst}}$
$(HO)_2P(O)CH_2NHCH_2CO_2H + CO_2 + HCHO$ Other by-products also may form, such as formic acid, which is formed by the oxidation of the formaldehyde by-product, and aminomethylphosphonic acid ("AMPA"), which is formed by the oxidation of N-(phosphonomethyl)glycine. The preference for heterogenous catalysis stems, at least in part, from the ease with which a particulate heterogeneous catalyst can normally be separated from the reaction product mixture for reuse following the oxidation. The literature is replete with examples of heterogeneous catalysts. See generally, Franz, et al., Glyphosate: A Unique Global Herbicide (ACS Monograph 189, 1997) at pp. 233–62 (and references cited therein); Franz, U.S. Pat. No. 3,950,402; Hershman, U.S. Pat. No. 3,969,398; Felthouse, U.S. Pat. No. 4,582,650; Chou, U.S. Pat. Nos. 4,624,937 and 4,696,772; Ramon et al., U.S. Pat. No. 5,179,228; and Ebner et al., U.S. Pat. No. 6,417,133.

High concentrations of formaldehyde in the reaction product mixture resulting from oxidative cleavage of an N-(phosphonomethyl)iminodiacetic acid substrate is undesirable. The formaldehyde by-product is undesirable because it reacts with N-(phosphonomethyl)glycine to produce unwanted by-products, mainly N-methyl-N-(phosphonomethyl)glycine ("NMG"), which reduce the N-(phosphonomethyl)glycine yield. In addition, the formaldehyde by-product itself is undesirable because of its potential toxicity. See Smith, U.S. Pat. No. 5,606,107.

Franz, U.S. Pat. No. 3,950,402, discloses oxidizing the formaldehyde by-product to carbon dioxide and water simultaneous with the oxidative cleavage of the N-(phosphonomethyl)iminodiacetic acid substrate by using a heterogenous oxidation catalyst comprising a noble metal deposited on a carbon support. The noble metal on carbon oxidation catalyst may be referred to as "bifunctional" since the carbon component provides the primary adsorption site for the oxidation of the N-(phosphonomethyl)iminodiacetic acid substrate to form the N-(phosphonomethyl)glycine product and formaldehyde, while the noble metal component provides the primary adsorption site for the oxidation of formaldehyde and formic acid to form carbon dioxide and water, thus giving the following reaction:

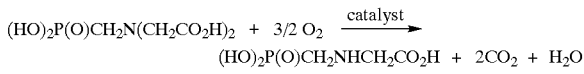

$(HO)_2P(O)CH_2N(CH_2CO_2H)_2 + 3/2\ O_2 \xrightarrow{\text{catalyst}}$
$(HO)_2P(O)CH_2NHCH_2CO_2H + 2CO_2 + H_2O$ The noble metal component may also tend to reduce the rate of deactivation of the catalyst (i.e., prolong the useful life of the catalyst). However, under typical conditions of the oxidation reaction, some of the noble metal in the catalyst used by Franz is oxidized into a more soluble form and both the N-(phosphonomethyl)iminodiacetic acid and N-(phosphonomethyl)glycine act as ligands which solubilize the noble metal. Thus, even though the process disclosed by Franz produces an acceptable yield and purity of N-(phosphonomethyl)glycine, high losses of the costly noble metal by dissolution into the aqueous reaction solution (i.e., "leaching") undermine the economic feasibility of the process.

Ramon et al., U.S. Pat. No. 5,179,228, disclose a process for the preparation of N-(phosphonomethyl)glycine by oxidation of N-(phosphonomethyl)iminodiacetic acid using an oxygen-containing gas in the presence of a noble metal on activated carbon catalyst. Recognizing the problem of leaching attendant the use of a noble metal on carbon catalyst in the oxidation of an N-(phosphonomethyl)iminodiacetic acid substrate (noble metal losses as great as 30% are reported), Ramon et al. propose flushing the reaction mixture with nitrogen gas under pressure after the oxidation reaction is complete. According to Ramon et al., nitrogen flushing causes redeposition of solubilized noble metal onto the surface of the carbon support and reduces the noble metal loss to less than 1%. However, the nitrogen flushing treatment taught by Ramon et al., which may last up to an hour, is conducted on the entire reaction mixture containing the N-(phosphonomethyl)glycine product in contact with the oxidation catalyst. Such prolonged contact after the oxidation reaction is complete may lead to considerable product losses through methylation as the N-(phosphonomethyl) glycine reacts with formaldehyde to produce N-methyl-N-(phosphonomethyl)glycine and other undesirable by-products. In addition, repeated dissolution and redeposition of the noble metal can lead to loss of noble metal surface area through sintering (i.e., the formation of undesirably thick layers or agglomerated clumps) which, in turn, decreases the activity of the catalyst.

More recently, attention has focused on developing bifunctional noble metal on carbon oxidation catalysts which resist noble metal leaching (i.e., exhibit improved compositional stability) and provide increased activity and/or selectivity, particularly with respect to oxidation of formaldehyde into carbon dioxide and water (i.e., increased formaldehyde activity). Ebner et al., U.S. Pat. No. 6,417,133, disclose so-called "deeply reduced" noble metal on carbon catalysts for use in the oxidative cleavage of an N-(phosphonomethyl)iminodiacetic acid substrate and oxidation of other oxidizable reagents and methods for their preparation. Such deeply reduced catalysts exhibit remarkable resistance to noble metal leaching in aqueous, acidic oxidation reaction media. As a result, the catalyst disclosed by Ebner at al. provides for substantially quantitative oxidation of N-(phosphonomethyl)iminodiacetic acid substrates to N-(phosphonomethyl)glycine products while maintaining effective oxidation of the formaldehyde and formic acid by-products of the reaction for a prolonged period and/or over numerous oxidation cycles.

Although the teachings of Ebner et al. are significant and make economically practical the otherwise unavailable advantages provided by noble metal on carbon catalysts in the preparation of N-(phosphonomethyl)glycine products by oxidative cleavage of N-(phosphonomethyl)iminodiacetic acid substrates, a need persists for improvements which might further reduce noble metal losses, provide increased catalyst stability and activity and/or selectivity, particularly in the oxidation of formaldehyde and other N-(phosphonomethyl)iminodiacetic acid substrate oxidation by-products, and generally extend the useful life of such catalysts.

SUMMARY OF THE INVENTION

Among the objects of the present invention, therefore, are the provision of improved processes for liquid phase oxidation of a reagent in an aqueous reaction mixture comprising contacting the aqueous reaction mixture containing the reagent with an oxygen-containing gas in the presence of a heterogenous oxidation catalyst comprising a noble metal deposited on a carbon support; the provision of such processes useful in the preparation of N-(phosphonomethyl) glycine products by oxidation of an N-(phosphonomethyl) iminodiacetic acid substrate; the provision of such processes wherein the catalyst exhibits improved stability and resistance to noble metal leaching; the provision of such processes wherein the catalyst activity and/or selectivity, particularly in the oxidation of formaldehyde, formic acid and other N-(phosphonomethyl)iminodiacetic acid substrate oxidation by-products, is maintained and the useful life of the catalyst is extended.

Briefly, therefore, the present invention is directed to a process for oxidizing a reagent in which an aqueous reaction mixture comprising the reagent and a heterogenous noble metal on carbon oxidation catalyst is contacted with an oxygen-containing gas in an oxidation reaction zone to oxidize the reagent. The resulting aqueous reaction product mixture comprises the oxidized reagent and the oxidation catalyst and has oxygen dissolved therein. At least a portion of the oxidized reagent is separated from the reaction product mixture to form a product fraction comprising the separated oxidized reagent substantially free of the oxidation catalyst and a catalyst slurry fraction comprising the oxidation catalyst in contact with a liquid medium having oxygen dissolved therein. The catalyst slurry fraction is subjected to a de-oxygenation treatment to reduce the dissolved oxygen concentration in the catalyst slurry fraction and the de-oxygenated catalyst slurry fraction is recycled and introduced into the oxidation reaction zone.

In another embodiment, the process comprises forming the aqueous reaction product mixture comprising the oxidized reagent and the oxidation catalyst by contacting the aqueous reaction mixture comprising the reagent and a heterogenous noble metal on carbon oxidation catalyst with an oxygen-containing gas in an oxidation reaction zone. A catalyst slurry comprising the oxidation catalyst in contact with a liquid medium is subjected to a de-oxygenation treatment comprising exposing the catalyst slurry to a non-oxidizing environment comprising a reducing gas. The oxidation catalyst obtained in the de-oxygenated catalyst slurry is recycled and introduced into the oxidation reaction zone.

In further embodiment, the present invention is directed to a process for the preparation of an N-(phosphonomethyl) glycine product. The process comprises contacting an aqueous reaction mixture comprising an N-(phosphonomethyl) iminodiacetic acid substrate and a heterogenous noble metal on carbon oxidation catalyst with an oxygen-containing gas in an oxidation reaction zone to oxidize the N-(phosphonomethyl)iminodiacetic acid substrate. The aqueous reaction product mixture produced comprises the N-(phosphonomethyl)glycine product and the oxidation catalyst. The reaction product mixture is filtered to separate at least a portion of the N-(phosphonomethyl)glycine product from the reaction product mixture and form a filtrate product fraction comprising the separated N-(phosphonomethyl)glycine product substantially free of the oxidation catalyst and a catalyst slurry fraction comprising the oxidation catalyst in contact with a liquid medium. The catalyst slurry fraction is subjected to a de-oxygenation treatment in which the catalyst slurry fraction is exposed to a non-oxidizing environment. The non-oxidizing environment may comprise a non-oxidizing gas and/or a reducing gas. The gas is introduced into a vessel containing the catalyst slurry fraction in a manner such that the gas introduced into the vessel passes through the catalyst slurry fraction. The de-oxygenated catalyst slurry fraction is recycled and introduced into the oxidation reaction zone.

Other objects and features of this invention will be in part apparent and in part pointed out hereinafter.

DETAILED DESCRIPTION OF THE PREFERRED EMBODIMENTS

Figure 1:
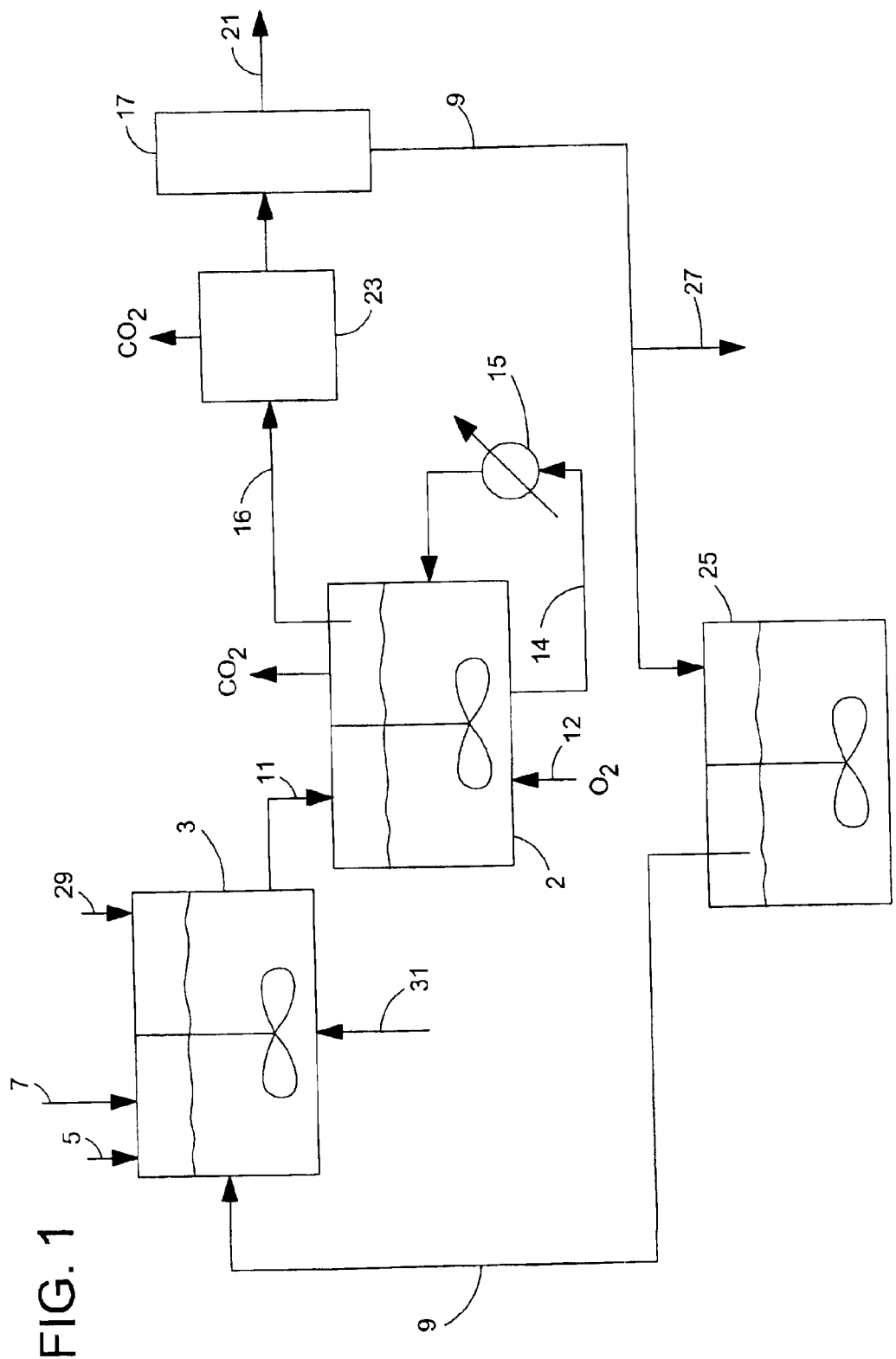
FIG. 1 is a schematic flow sheet of a continuous oxidation reactor system for oxidizing an N-(phosphonomethyl) iminodiacetic acid substrate to form an N-(phosphonomethyl)glycine product and including a de-oxygenation stage for de-oxygenating a heterogeneous particulate catalyst slurry recycled in a loop independent from a heat transfer recirculation loop and including a flash tank and catalyst recycle tank.

In liquid phase oxidation of a reagent in an aqueous reaction mixture contacted with an oxygen-containing gas in the presence of a heterogenous noble metal on carbon oxidation catalyst, the noble metal catalyst tends to deactivate over time, both in continuous processing as well as from batch to batch, such that there is a practical limit to the recycling and reuse of the catalyst. Deactivation is attributable to a variety of phenomena. In accordance with the present invention, it has been discovered that one mechanism by which noble metal on carbon catalysts used to catalyze liquid phase oxidation of reagents with molecular oxygen may be deactivated is the adsorption of oxygen onto the surface of the supported noble metal. Adsorption includes both physisorption and chemisorption. Physisorbed oxygen is simply molecular oxygen adhered to the surface of the noble metal or otherwise present in the crystal lattice of the noble metal, while chemisorption involves bond formation between oxygen and oxidized noble metal atoms. For example, elemental platinum, $Pt^0$, may be oxidized to catalytically inert $Pt^{4+}$ in platinum dioxide ($PtO_2$) which is more readily leached or solubilized into the aqueous reaction mixture. Moreover, physisorbed and chemisorbed oxygen on noble metal on carbon catalyst reduces catalytic activity by hindering access of the reagent to catalytic sites on the surface and within the crystal lattice of the noble metal.

It has been discovered that the deactivating effects of oxygen adsorbed onto heterogenous noble metal on carbon oxidation catalysts used in liquid phase oxidation reactions can be alleviated and the useful life of the catalyst extended by periodically subjecting the catalyst to a de-oxygenation treatment. The de-oxygenation treatment in accordance with the present invention can be applied generally to noble metal on carbon catalysts used to catalyze the oxidation of a wide variety of reagents in a liquid reaction mixture contacted with an oxygen-containing gas. For example, the present invention has application in treating noble metal on carbon catalysts used to catalyze the oxidation of an N-substituted-N-(phosphonomethyl)glycine substrate (e.g., N-methyl-N-(phosphonomethyl)glycine) to produce N-(phosphonomethyl)glycine as disclosed, for example, by Morgenstern et al., U.S. Pat. Nos. 6,005,140 and 6,232,494, the entire disclosures of which are incorporated herein by reference. However, the present invention has particular application in treating noble metal on carbon catalysts used in the preparation of an N-(phosphonomethyl)glycine product (i.e., N-(phosphonomethyl)glycine, a salt of N-(phosphonomethyl)glycine, or an ester of N-(phosphonomethyl)glycine) by catalytic oxidation of an N-(phosphonomethyl)iminodiacetic acid substrate (i.e., N-(phosphonomethyl)iminodiacetic acid, a salt of N-(phosphonomethyl)iminodiacetic acid, or an ester of N-(phosphonomethyl)iminodiacetic acid) and the resulting formaldehyde and formic acid by-products in an aqueous reaction mixture as disclosed, for example, by Ebner et al., U.S. Pat. No. 6,417,133 and Haupfear et al., U.S. Published Application No. US 2002/0068836 A1, the entire disclosures of which are incorporated herein by reference. The present invention also has application in treating noble metal on carbon catalysts used to oxidize formaldehyde and formic acid present in aqueous waste streams generated upon purification of the N-(phosphonomethyl)glycine product as disclosed, for example, by Smith in U.S. Pat. No. 5,606,107, the entire disclosure of which is incorporated herein by reference.

In the following description of the practice of the present invention, particular reference will be made to its application in the preparation of an N-(phosphonomethyl)glycine product by oxidative cleavage of a carboxymethyl substituent from an N-(phosphonomethyl)iminodiacetic acid substrate in an aqueous reaction mixture using an oxygen-containing gas in the presence of a noble metal on carbon catalyst. It should be recognized, however, that the principles disclosed herein are generally applicable to other liquid phase oxidative reactions in which a reagent is oxidized with an oxygen-containing gas in the presence of a noble metal on carbon catalyst, especially those conducted in aqueous reaction mixtures and those in which the catalyst is susceptible to deactivation by adsorbed oxygen. The adaptation of the present invention to treat noble metal on carbon catalysts used to catalyze the same reagents in other contexts or other liquid phase oxidation reactions altogether will be readily apparent to those skilled in the art.

A wide variety of heterogenous bifunctional oxidation catalysts comprising one or more noble metals on the surface of a carbon support are known for catalyzing the liquid phase oxidation of an N-(phosphonomethyl) iminodiacetic acid substrate to prepare N-(phosphonomethyl)glycine and related compounds.

In general, the carbon support used in the present invention are well known in the art. Activated, non-graphitized carbon supports are preferred. These supports are characterized by high adsorptive capacity for gases, vapors, and colloidal solids and relatively high specific surface areas. The support suitably may be a carbon, char, or charcoal produced by means known in the art, for example, by destructive distillation of wood, peat, lignite, coal, nut shells, bones, vegetable, or other natural or synthetic carbonaceous matter, but preferably is activated to develop adsorptive power. Activation usually is achieved by heating to high temperatures (800–900° C.) with steam or with carbon dioxide which brings about a porous particle structure and increased specific surface area. In some cases, hygroscopic substances, such as zinc chloride and/or phosphoric acid or sodium sulfate, are added before the destructive distillation or activation, to increase adsorptive capacity. Preferably, the carbon content of the carbon support ranges from about 10% for bone charcoal to about 98% for some wood chars and nearly 100% for activated carbons derived from organic polymers. The non-carbonaceous matter in commercially available activated carbon materials normally will vary depending on such factors as precursor origin, processing, and activation method. Many commercially available carbon supports contain small amounts of metals. Carbon supports having the fewest oxygen-containing functional groups at their surfaces are most preferred.

In a particularly preferred embodiment, the support is in the form of particulates. Suitable particulate supports may have a wide variety of shapes. For example, such supports may be in the form of pellets, granules and powders. Pellet supports typically have a particle size of from about 1 mm to about 10 mm. Preferably, the support is in the form of a powder. These particulate supports may be used in a reactor system as free particles suspended in the aqueous reaction mixture. Typically, the particulate carbon support may include a broad size distribution of particles. For powders, preferably at least about 95% of the particles are from about 2 to about 300 μm in their largest dimension, more preferably at least about 98% of the particles are from about 2 to about 200 μm in their largest dimension, and most preferably about 99% of the particles are from about 2 to about 150 μm in their largest dimension with about 95% of the particles being from about 3 to about 100 μm in their largest dimension. Preferably, the average particle size of the particulate catalyst is from about 15 to about 40 μm, more preferably about 25 μm.

The specific surface area of the carbon support, measured by the BET (Brunauer-Emmett-Teller) method using nitrogen, is preferably from about 10 to about 3,000 M²/g (surface area of carbon support per gram of carbon support), more preferably from about 500 to about 2,100 m²/g, and still more preferably from about 750 to about 2,100 m²/g. In some embodiments, the most preferred specific area is from about 750 to about 1,750 m²/g. The pore volume of the support may vary widely.

Suitable carbon supports are commercially available from a number of sources. The following is a listing of some of the activated carbons which may be used with this invention: Darco G-60 Spec and Darcox(ICI-America, Wilmington, Del.); Norit SG Extra, Norit EN4, Norit EXW, Norit A, Norit Ultra-C, Norit ACX, and Norit 4×14 mesh (Amer. Norit Co., Inc., Jacksonville, Fla.); Gl-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar CN, Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); and Columbia SXAC (Union Carbide New York, N.Y.).

The carbon support has one or more noble metal(s) at its surface. Preferably, the noble metal(s) is selected from the group consisting of platinum (Pt), palladium (Pd), ruthenium (Ru), rhodium (Rh), iridium (Ir), silver (Ag), osmium (Os), and gold (Au). In general, platinum and palladium are more preferred, and platinum is especially preferred. It should be understood that the term noble metal as used herein means the noble metal in its elemental state as well as the noble metal in any of its various oxidation states. In addition to the noble metal, at least one promoter may be at the surface of the carbon support (i.e., a catalyst-surface promoter). As used herein, a promoter is a metal that tends to increase catalyst selectivity, activity, and/or stability. A promoter additionally may reduce noble metal leaching. Although the promoter usually is deposited onto the surface of the carbon support in a promoter deposition step, the carbon support itself may also (or alternatively) naturally contain a promoter. The catalyst-surface promoter may, for example, be an additional noble metal(s) at the surface of the carbon support. For example, depending on the application, ruthenium and palladium may act as catalyst-surface promoters on a catalyst comprising platinum deposited at a carbon support surface. The catalyst-surface promoter(s) alternatively may be, for example, a metal selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn), cerium (Ce), zirconium (Zr), tellurium (Te), and germanium (Ge). Preferably, the catalyst-surface promoter is selected from the group consisting of bismuth, iron, tin, tellurium and titanium. In a particularly preferred embodiment, the catalyst-surface promoter is tin. In another particularly preferred embodiment, the catalyst-surface promoter is iron. In an additional preferred embodiment, the catalyst-surface promoter is titanium. In a further particularly preferred embodiment, the catalyst comprises both iron and tin at its surface. Use of iron, tin, or both generally (1) reduces noble metal leaching during prolonged use of a catalyst (e.g., a catalyst used over several oxidation reaction cycles), and (2) tends to increase and/or maintain the activity of the catalyst when the catalyst is used to effect the oxidation of an N-(phosphonomethyl)iminodiacetic acid substrate. Catalysts comprising iron generally are most preferred because they tend to have the greatest activity and stability with respect to formaldehyde and formic acid oxidation. Preferably, the noble metal is alloyed with at least one catalyst-surface promoter to form alloyed metal particles at the surface of the carbon support. In accordance with an especially preferred embodiment, the heterogenous catalyst used in the liquid phase oxidative cleavage of the N-(phosphonomethyl)iminodiacetic acid substrate is a "deeply reduced" catalyst as described by Ebner et al. in U.S. Pat. No. 6,417,133 and in U.S. Published Application No. US 2002/0068836 A1 (Haupfear et al.) comprising a noble metal deposited on a particulate carbon support and including a catalyst-surface promoter. However, it should be understood that the advantages provided by the de-oxygenation treatment of the present invention are attainable with respect to a wide assortment of commercially available noble metal on carbon catalysts.

As is recognized in the art, liquid phase oxidation of N-(phosphonomethyl)iminodiacetic acid substrates may be carried out in a batch, semi-batch or continuous reactor system containing one or more oxidation reaction zones. The oxidation reaction zone(s) may be suitably provided by various reactor configurations, including those that have back-mixed characteristics, in the liquid phase and optionally in the gas phase as well, and those that have plug flow characteristics. Suitable reactor configurations having back-mixed characteristics include, for example, stirred tank reactors, ejector nozzle loop reactors (also known as venturi-loop reactors) and fluidized bed reactors. Suitable reactor configurations having plug flow characteristics include those having a packed or fixed catalyst bed (e.g., trickle bed reactors and packed bubble column reactors) and bubble slurry column reactors. Fluidized bed reactors may also be operated in a manner exhibiting plug flow characteristics. The configuration of the reactor system and the number of oxidation reaction zones is not critical to the practice of the present invention. However, it is preferred that the oxidation reactor system employed be adapted for use of a noble metal on carbon catalyst suspended in the aqueous reaction mixture and include a filter to separate at least a portion of the N-(phosphonomethyl)glycine product from the reaction product mixture comprising the N-(phosphonomethyl) glycine product and the particulate catalyst such that the resulting catalyst slurry fraction comprising the particulate catalyst can be recycled and reintroduced into the oxidation reaction zone(s).

Likewise, conditions, including temperature and pressure maintained in the oxidation reaction zone(s), reagent concentration, catalyst loading or concentration, reaction time, etc., suitable for liquid phase oxidative cleavage of a carboxymethyl substituent from an N-(phosphonomethyl) iminodiacetic acid substrate in an aqueous reaction mixture using an oxygen-containing gas in the presence of a noble metal on carbon catalyst are well known to those skilled in the art and the selection of these variables is not affected by the practice of the present invention.

Oxidation of the N-(phosphonomethyl)iminodiacetic acid substrate may be conducted at a wide range of temperatures, and at pressures ranging from sub-atmospheric to super-atmospheric. Operating at higher temperatures and super-atmospheric pressures, while increasing plant costs, is preferred since such conditions tend to improve phase transfer between the liquid and gas phase and increase the oxidation reaction rate. Moreover, the temperature within the oxidation reaction zone is preferably maintained sufficiently high with respect to the N-(phosphonomethyl)glycine product concentration such that essentially all the N-(phosphonomethyl)glycine product in the reaction product mixture is dissolved. The temperature of the aqueous reaction mixture contacted with the oxygen-containing gas is suitably from about 80 to about 180° C., preferably from about 90 to about 150° C., and more preferably from about 95 to about 110° C. The pressure maintained within the oxidation reaction zone(s) generally depends on the temperature of the aqueous reaction mixture. Preferably, the pressure is sufficient to prevent the reaction mixture from boiling and is adequate to cause the oxygen from the oxygen-containing gas to dissolve into the reaction mixture at a rate sufficient such that oxidation of the N-(phosphonomethyl)iminodiacetic acid substrate is not limited due to an inadequate oxygen supply. Suitable pressures range from about 30 to about 500 psig, and preferably from about 30 to about 130 psig. The concentration of the particulate catalyst and the N-(phosphonomethyl) iminodiacetic acid substrate in the aqueous reaction mixture are not critical. Typically, the catalyst concentration is from about 0.1 to about 10% by weight ([mass of catalyst÷total reaction mass]×100%). Preferably, the catalyst concentration is from about 0.2 to about 5%, and more preferably from about 1 to about 4% by weight. Concentrations greater than about 10% are difficult to separate from the N-(phosphonomethyl)glycine product. On the other hand, concentrations less than about 0.1% tend to produce unacceptably low reaction rates. The concentration of N-(phosphonomethyl)iminodiacetic acid substrate is preferably selected such that all reactants and the N-(phosphonomethyl)glycine product remain in solution so that the suspended particulate catalyst can be recovered for re-use, for example, by filtration. Normally, the concentration of N-(phosphonomethyl)iminodiacetic acid substrate is up to about 25% by weight ([mass of N-(phosphonomethyl) iminodiacetic acid substrate÷total reaction mass]×100%), and with respect to the preferred temperatures of the aqueous reaction mixture, preferably from about 7 to about 15% by weight. The pH of the aqueous reaction mixture is typically less than about 7 and often in the range of from about 1 to about 2. When conducted in a continuous reactor system, the residence time in the oxidation reaction zone can vary widely depending on the specific catalyst employed, catalyst concentration and other conditions. Typically, the residence time can vary over the range of from about 3 to about 120 minutes. Preferably, the residence time is from about 5 to about 90 minutes, and more preferably from about 5 to about 60 minutes. When conducted in a batch reactor system, the reaction time typically varies over the range of from about 15 to about 120 minutes. Preferably, the reaction time is from about 20 to about 90 minutes, and more preferably from about 30 to about 60 minutes.

The oxygen-containing gas used for oxidation of the N-(phosphonomethyl)iminodiacetic acid substrate is any gaseous mixture comprising molecular oxygen which optionally may comprise one or more diluents which are non-reactive with the oxygen or with the substrate or oxidation product under the reaction conditions. Examples of such gases are air, pure molecular oxygen, or molecular oxygen diluted with helium, argon, nitrogen, or other non-oxidizing gases. For economic reasons, the oxygen source is usually air or pure molecular oxygen. Preferably, the oxygen-containing gas comprises at least about 95 mole % $O_2$, typically approximately 98 mole % $O_2$. The oxygen may be contacted with the aqueous reaction mixture by any conventional means in a manner which maintains the dissolved oxygen concentration in the reaction mixture at the desired level and preferably in a manner which maximizes the contact of the gas with the reaction solution. Such contact may be obtained, for example, by dispersing the gas through a diffuser such as a porous frit or sparger immersed in the reaction mixture. The oxygen feed rate preferably is such that oxidation of the N-(phosphonomethyl) iminodiacetic acid substrate is not limited by oxygen supply, but not too high so as to lead to detrimental oxidation of the surface of the noble metal on carbon catalyst.

Suitable reactor systems and oxidation reaction conditions for liquid phase catalytic oxidation of an N-(phosphonomethyl)iminodiacetic acid substrate are described, for example, by Ebner et al., U.S. Pat. No. 6,417,133 and Haupfear et al., U.S. Published Application No. US 2002/0068836 A1.

For purpose of illustration, de-oxygenation of a noble metal on carbon catalyst in accordance with the present invention will be described in connection with the oxidation reactor system depicted in FIG. 1. FIG. 1 is a schematic flow sheet of an oxidation reactor system comprising a single continuous oxidation reaction zone for the liquid phase oxidation of an N-(phosphonomethyl)iminodiacetic acid substrate to form an N-(phosphonomethyl)glycine product in which a noble metal on carbon particulate catalyst slurry is recycled in a loop independent from a heat transfer recirculation loop and including a flash tank and catalyst recycle tank. The oxidation reactor system further includes a de-oxygenation stage for de-oxygenating the recycled heterogeneous particulate catalyst slurry.

The reactor system shown in FIG. 1 comprises a continuous stirred tank reactor 2 providing mechanical agitation of the aqueous liquid reaction mixture contained therein, typically by a rotating impeller. Stirred tank reactors suitably back-mix the liquid phase within the reaction zone, are relatively simple in design and operation and can be scaled to the desired process capacity. Various impeller designs may be employed, including systems with multiple blades rotated on a common shaft. The reactor vessel may include internal baffles and/or draft tubes to modify mixing characteristics and prevent swirling of the aqueous reaction mixture as is well-known to those skilled in the art. Although the reactor system shown in FIG. 1 comprises a single continuous stirred tank reactor, a reactor system comprising two or more back-mixed oxidation reaction zones staged in series may be employed. A combination of two or more back-mixed oxidation reaction zones in series is advantageous because such a reactor system tends to behave more like a plug flow reactor, producing fewer by-products and improving the yield of the N-(phosphonomethyl)glycine product. Moreover, the combination of two or more reaction zones provides the ability to vary reaction conditions in accord with the prevailing reaction kinetics at different stages of the oxidation reaction. The second and subsequent oxidation reaction zone(s) may provide further conversion of N-(phosphonomethyl)iminodiacetic acid substrate and/or oxidation of formaldehyde and formic acid by-products. The back-mixed oxidation reaction zone(s) may be suitably provided by reactor configurations other than continuous stirred tank reactors (e.g., ejector nozzle loop reactors and fluidized bed reactors). Moreover, different reactor configurations may be combined in a reactor system comprising multiple oxidation reaction zones. For example, one or more reactors having back-mixed characteristics may be combined with a reactor configuration having plug flow characteristics such as a fixed catalyst bed reactor.

As shown in FIG. 1, a reactor feed tank 3 may be used to mix a source of the N-(phosphonomethyl)iminodiacetic acid substrate 5 (e.g., N-(phosphonomethyl)iminodiacetic acid slurry), process water 7 and recycled particulate catalyst in stream 9 to form an aqueous feed stream 11 of the desired composition introduced into reactor 2. In addition to water, other reaction solvents may also be present along with various recycle streams from concentrating and purifying the N-(phosphonomethyl)glycine product. The reactor feed tank, like the stirred tank reactor, is provided with a rotating impeller or other suitable means for agitating the feed mixture prepared therein. A molecular oxygen-containing gas 12 is also introduced into the oxidation reaction zone within the stirred tank reactor. The oxygen-containing gas is introduced into the reaction mixture in a manner which provides intimate contact of the gas with the reaction mixture. For example, an oxygen-containing gas may be introduced through a sparger conduit or similar distributor positioned in the bottom of the stirred tank reactor below the impeller so that the turbulence induced by the rotating impeller intimately mixes and distributes the oxygen-containing gas as it rises though the reaction mixture. Distribution of the oxygen-containing gas within the reaction mixture may be further enhanced by passing the gas through a diffuser such as a porous frit or by other means well-known to those skilled in the art. Alternatively, the oxygen-containing gas may be introduced into the head space above the reaction mixture in the stirred tank reactor.

If the dissolved oxygen concentration in the reaction mixture is too great, the catalyst surface tends to become detrimentally oxidized, which, in turn, tends to lead to increased noble metal leaching, decreased formaldehyde oxidation activity and increased production of N-methyl-N-(phosphonomethyl)glycine. To avoid this problem, it is generally preferred to use an oxygen feed rate such that at least about 40%, more preferably at least about 60%, even more preferably at least about 80%, and still even more preferably at least about 90% of the oxygen is utilized. As used herein, the percentage of oxygen utilized equals: (the total oxygen consumption rate÷oxygen feed rate)×100%. The term total oxygen consumption rate means the sum of: (i) the oxygen consumption rate ($R_i$) of the oxidation reaction of the N-(phosphonomethyl)iminodiacetic acid substrate to form the N-(phosphonomethyl)glycine product and formaldehyde, (ii) the oxygen consumption rate ($R_{ii}$) of the oxidation reaction of formaldehyde to form formic acid, and (iii) the oxygen consumption rate ($R_{iii}$) of the oxidation reaction of formic acid to form carbon dioxide and water. The oxygen partial pressure may vary in different regions of the oxidation reaction zone. Preferably, the oxygen partial pressure in the head space above the liquid reaction mixture in stirred tank reactor 2 is from about 0.1 to about 35 psia, more preferably from about 1 to about 10 psia.

An aqueous reaction mixture comprising the N-(phosphonomethyl)iminodiacetic acid substrate and having the heterogenous particulate catalyst suspended therein is continuously contacted with the oxygen-containing gas 12 introduced into the oxidation reaction zone defined within stirred tank reactor 2. Vapor comprising carbon dioxide evolved as the formaldehyde by-product is further oxidized in the presence of the noble metal on carbon catalyst is vented from the head space above the reaction mixture in the stirred tank reactor. Because the oxidation reaction is exothermic, it will normally be necessary to remove heat energy from the aqueous reaction mixture once the oxidation reaction begins to evolve significant amounts of heat in order to maintain the desired temperature within the oxidation zone. As shown in FIG. 1, excess reaction heat may be extracted from the reaction mixture within stirred tank reactor 2 by passing the reaction mixture through an external heat transfer recirculation loop 14 containing a heat exchanger 15 wherein heat is transferred indirectly from the reaction mixture to a cooling medium (e.g., cooling water). The reaction temperature is controlled by, for example, controlling the supply of cooling water to heat exchanger 15 in response to the signal from a temperature controller. Reaction heat can be removed from the oxidation reaction zone by other conventional means as well, such as with cooling coils immersed within the reaction mixture or a reactor vessel jacket through which a cooling medium is circulated.

An aqueous reaction product mixture 16 containing the N-(phosphonomethyl)glycine product, the noble metal on carbon catalyst and dissolved oxygen is continuously or intermittently withdrawn from stirred tank reactor 2. Typically, the concentration of the N-(phosphonomethyl)glycine product in the reaction product mixture may be as great as 40% by weight, or greater. Preferably, the N-(phosphonomethyl)glycine product concentration is from about 5 to about 40%, more preferably from about 8 to about 30%, and still more preferably from about 9 to about 15%. Concentrations of formaldehyde in the product mixture are typically less than about 0.5% by weight, more preferably less than about 0.3%, and still more preferably less than about 0.15%. The reaction product mixture withdrawn from stirred tank reactor 2 is transferred to a catalyst filter 17 wherein at least a portion of the N-(phosphonomethyl)glycine product is separated to form: (1) a product fraction (i.e., filtrate) 21 containing much of the N-(phosphonomethyl)glycine product substantially free of the noble metal on carbon oxidation catalyst; and (2) a catalyst slurry fraction 9 comprising substantially all the catalyst particles suspended in an aqueous liquid medium comprising a residual amount of the N-(phosphonomethyl)glycine product and unreacted N-(phosphonomethyl)iminodiacetic acid substrate.

Catalyst filter 17 used to separate the particulate catalyst from the reaction product mixture 16 withdrawn from stirred tank reactor 2 is preferably a filter adapted for continuous separation of catalyst from the reaction mixture. That is, the catalyst filter is capable of receiving a continuous flow of reaction mixture and continuously forming the product fraction and the catalyst slurry fraction without having to interrupt the flow of reaction mixture introduced into the filter. Suitable continuous catalyst filtration systems include continuous cross-flow filters and, more preferably, continuous back-pulse filters. A continuous back-pulse filter system comprises a filter element and is preferably operated adiabatically, but may be provided with heating or cooling capability. Preferably, the liquid used to back-pulse the filter element and remove separated catalyst is a portion of the filtrate product fraction. In typical operation, a back-pulse filter might increase the concentration of the noble metal on carbon catalyst particles from about 4% by weight in the reaction product mixture to from about 10 to about 30% by weight in the catalyst slurry fraction.

Aside from cross-flow and back-pulse filters, the catalyst filter used in a continuous oxidation reactor system may alternatively be a vacuum filter or may comprise a bank of leaf filters used to treat a continuous flow of reaction product mixture in staggered filtration cycles. As a further alternative, stirred tank reactor 2 may include an internal catalyst filter (e.g., a porous frit) which blocks the particulate catalyst from being withdrawn from the reactor as part of the product fraction such that the catalyst is substantially retained within the oxidation reaction zone and the product fraction is substantially free of the particulate catalyst. Moreover, it should be recognized that other means of catalyst separation may be used instead of (or in addition to) the catalyst filter 17. For example, the catalyst could be separated from the oxidation reaction product mixture using a centrifuge.

When the operating total pressure in the oxidation reaction zone is much higher than atmospheric pressure, as is preferred, the pressure over the reaction product mixture 16 withdrawn from stirred tank reactor 2 is typically reduced in connection with concentrating and purifying the N-(phosphonomethyl)glycine product. As shown in FIG. 1, at least a portion of this pressure reduction may take place in a flash tank 23 upstream of catalyst filter 17. The flash tank lowers the pressure on the reaction product mixture to some degree, causing dissolved carbon dioxide to be flashed out of the mixture and vented as vapor from the flash tank. Flash tank 23 reduces the pressure at which the catalyst filter 17 must operate, thereby reducing the capital costs and complexity of the filter system.

The filtrate product fraction 21 substantially free of catalyst is carried forward to concentrate and purify the N-(phosphonomethyl)glycine product (e.g., by evaporation) as is well-known to those skilled in the art. The catalyst slurry fraction 9 is continuously withdrawn from catalyst filter 17 and recycled to reactor feed tank 3 through an optional catalyst holding tank 25 (also called a catalyst recycle tank or catalyst slurry tank) before the recycled catalyst is reintroduced into the oxidation reaction zone within stirred tank reactor 2. The catalyst holding tank or catalyst recycle tank 23 may have various configurations, but is typically a stirred tank in which the catalyst slurry comprising the particulate catalyst and residual reaction mixture is agitated with a rotating impeller to improve uniformity in the catalyst slurry by preventing the catalyst from settling.

As the noble metal on carbon catalyst deactivates with use (e.g., exhibits diminished activity and/or selectivity), the catalyst may be continuously or intermittently purged from the continuous oxidation reactor system via a catalyst purge stream 27, and replaced with fresh catalyst via a fresh catalyst feed stream 29 introduced into reactor feed tank 3. When intermittently purging the catalyst, the entire catalyst mass may be purged from the process at the same time (which is typically the more preferred method), or a fraction of the catalyst mass may be purged at various time increments. In other words, intermittent purging includes any repeated purging of catalyst that is not continuous.

The noble metal on carbon catalyst is at least partially reactivated, either continuously or intermittently, using various techniques, including the de-oxygenation treatment in accordance with the present invention described in detail below. In addition to the de-oxygenation treatment, other techniques for reactivating the catalyst may be employed. For example, reactivation may include introducing a supplemental promoter such as bismuth oxide ($Bi_2O_3$) into the reactor system as disclosed, in U.S. Published Application No. US 2002/0068836 A1 (Haupfear et al.) and U.S. Published Application No. 2002/0016503 (Leiber et al.), the entire disclosure of which is incorporated herein by reference.

The de-oxygenation treatment may be suitably carried out by exposing the noble metal on carbon catalyst to a non-oxidizing environment (i.e., an environment essentially free of oxygen) in a de-oxygenation stage. Preferably, the catalyst is de-oxygenated while in contact with a liquid medium which may include other components of the aqueous reaction mixture in which oxidation of the reagent takes place. For example, the reaction product mixture 16 withdrawn from stirred tank reactor 2 or the catalyst slurry fraction 9 containing the catalyst particles dispersed or suspended in an aqueous liquid medium may suitably be subjected to the de-oxygenation treatment. In accordance with an especially preferred embodiment, the noble metal on carbon oxidation catalyst is subjected to de-oxygenation after at least a portion of the N-(phosphonomethyl)glycine product has been separated from the reaction product mixture withdrawn from the oxidation reaction zone. For example, in FIG. 1, the catalyst suspended in the catalyst slurry fraction 9 is subjected to the de-oxygenation treatment.

The non-oxidizing environment may consist essentially of a non-oxidizing gas. The noble metal on carbon catalyst suspended in the catalyst slurry may be exposed to the non-oxidizing environment by introducing a non-oxidizing gas into a vessel (e.g., reactor feed tank 3 or catalyst recycle tank 25) or conduit containing the slurry as it is recycled from catalyst filter 17 to the oxidation reaction zone within reactor 2. A suitable non-oxidizing gas includes nitrogen ($N_2$), argon (Ar), helium (He) and mixtures thereof. In accordance with a preferred embodiment, the non-oxidizing gas consists essentially of nitrogen. Preferably, the non-oxidizing gas is introduced into the catalyst slurry in a manner which provides intimate contact of the gas with the catalyst particles suspended in the liquid medium and promotes vigorous agitation of the suspended catalyst particles to facilitate dislodgement and removal of molecular oxygen from the slurry (i.e., in much the same manner as the oxygen-containing gas is contacted with the aqueous reaction mixture within the oxidation reaction zone). Accordingly, non-oxidizing gas from a pressurized source may be introduced through a small orifice nozzle, sparger conduit, dip tube or similar distributor positioned near the bottom of reactor feed tank 3 or catalyst recycle tank 25 below the impeller so that the turbulence induced by the rotating impeller intimately mixes and distributes the non-oxidizing gas through the catalyst slurry. Likewise, distribution of the non-oxidizing gas within the catalyst slurry may be further enhanced by passing the gas through a diffuser such as a porous frit or by other means well-known to those skilled in the art for promoting gas-liquid phase contact. As bubbles of the non-oxidizing gas pass through the agitated catalyst slurry, it dislodges molecular oxygen adsorbed on the surface of or otherwise entrapped in the catalyst structure so that it is freed and purged from the liquid medium in contact with the particulate catalyst and the vessel becomes filled with a non-oxidizing atmosphere. Following the de-oxygenation treatment, the de-oxygenated catalyst slurry fraction is recycled and introduced into the oxidation reaction zone.

In the preferred embodiment shown in FIG. 1, a non-oxidizing gas 31 from a pressurized source (not shown) is introduced near the bottom of reactor feed tank 3 which also serves as the de-oxygenation stage. The reactor feed tank is vented to allow the non-oxidizing gas, liberated molecular oxygen and other purged components of the catalyst slurry (i.e., the aqueous feed mixture) to pass through the head space above the slurry and be expelled to an appropriate vapor recovery system (not shown). By conducting the de-oxygenation treatment in the reactor feed tank, the benefits of de-oxygenation on catalyst performance are realized immediately prior to introducing the de-oxygenated catalyst slurry fraction into the oxidation reaction zone. Alternatively, the non-oxidizing gas may suitably be introduced into catalyst recycle tank 25. However, this alternative is less preferred since the concentration of N-(phosphonomethyl)glycine product and unreacted N-(phosphonomethyl)iminodiacetic acid substrate in the catalyst slurry fraction is typically significantly higher as compared to the concentration in the feed mixture prepared in reactor feed tank 3 and cooling effects accompanying introduction of the non-oxidizing gas may risk undesired precipitation of these components absent special precautions. In an even less preferred embodiment, the non-oxidizing gas may be introduced into the head space above the catalyst slurry in reactor feed tank 3 or catalyst recycle tank 25.

Wherever the catalyst de-oxygenation stage is located, the treatment is preferably carried out continuously on at least a portion of the catalyst charged to the reactor system so as to obtain the maximum beneficial effects. The de-oxygenation treatment, whether conducted continuously or intermittently, improves catalyst performance by removing physisorbed oxygen from the catalyst surface and inhibiting chemisorption of oxygen on the catalyst surface and oxidation of the noble metal which can lead to increased noble metal leaching. Noble metal loss is detrimental to formaldehyde and formic acid oxidation activity, which increases production of undesired by-products and decreases N-(phosphonomethyl) glycine product yield. Moreover, removal of dissolved oxygen adsorbed on the surface of the catalyst provides improved access for the formaldehyde and formic acid by-products to catalyst sites.

Although the de-oxygenation stage for the noble metal on carbon catalyst is shown in FIG. 1 in the context of a continuous oxidation reactor system, it can be readily adapted for application in a batch or semi-batch oxidation reaction process. In batch and semi-batch operations, after the desired conversion in the oxidation reaction is attained, reaction product mixture comprising the oxidized reagent and the noble metal on carbon catalyst is typically transferred from the oxidation reaction zone (e.g., a stirred tank reactor) to a suitable catalyst filter (e.g., a leaf filter) to separate at least a portion of the oxidized reagent and form a product fraction substantially free of the particulate catalyst and a catalyst slurry fraction comprising substantially all of the oxidation catalyst and optionally sluice water used to remove the separated catalyst from the filter. The catalyst slurry fraction is then usually sluiced to a catalyst recycle tank until the catalyst mass is again required to catalyze the oxidation of additional reagent in a succeeding batch. As described above in connection with FIG. 1, the catalyst recycle tank is typically has a rotating impeller or similar means to agitate the catalyst slurry fraction and keep the particulate catalyst uniformly dispersed in the slurry and may further include a circulation loop with a pump through which catalyst slurry retained in the catalyst recycle tank is circulated. The catalyst recycle tank used in such batch and semi-batch operations is a suitable vessel for conducting the catalyst de-oxygenation treatment in accordance with the present invention. For example, the non-oxidizing gas from a pressurized source may be sparged or injected into the catalyst slurry near the bottom of the catalyst recycle tank beneath the rotating impeller. It may be necessary to shut down the circulation pump during the de-oxygenation treatment to avoid cavitation. Although less preferred, the de-oxygenation treatment in connection with a batch or semi-batch oxidation process can be also performed on the catalyst in the aqueous reaction product mixture prior to filtration (e.g., by sparging or injecting the non-oxidizing gas into the aqueous reaction product mixture in the oxidation reactor after the conclusion of the oxidation reaction). In accordance with a preferred embodiment, the catalyst is subjected to the de-oxygenation treatment after the first and each succeeding oxidation reaction batch in order to obtain the maximum beneficial effects. Moreover, in connection with a batch or semi-batch oxidation reactor system, it is preferred to subject the catalyst to the de-oxygenation treatment just prior to reusing the de-oxygenated catalyst in the succeeding oxidation reaction batch.

Regardless of whether the oxidation reactor system is operated continuously or in a batch or semi-batch mode, the de-oxygenation stage is preferably operated at a pressure at or near atmospheric pressure, although it may be advantageous to moderately pressurize the catalyst slurry during de-oxygenation using the non-oxidizing gas.

The temperature of the catalyst slurry during the de-oxygenation treatment is not narrowly critical. Preferably, the de-oxygenation stage is operated adiabatically and the catalyst slurry is maintained at a temperature during the de-oxygenation treatment consistent with overall process objectives (e.g., avoiding the precipitation of components of the catalyst slurry and providing de-oxygenated catalyst slurry at a temperature appropriate for recycle and reintroduction into the oxidation reaction zone).

Generally, increasing the rate at which the non-oxidizing gas is introduced into the catalyst slurry enhances the beneficial effects of the de-oxygenation treatment. For a typical plant scale application in which 32,000 lbs (14,550 kg) of a catalyst slurry containing from about 2 to about 30% by weight of the noble metal catalyst is de-oxygenated, suitable results may be achieved by introducing nitrogen or other non-oxidizing gas into the catalyst slurry at a rate of from about 10 to about 120 standard $ft^3$/min (about 15 to about 185 $m^3$/hr). Similarly, catalyst performance is generally enhanced by extending the duration of the de-oxygenation treatment. However, other process considerations (e.g., throughput and demand for the recycled de-oxygenated catalyst slurry in the oxidation reaction zone) typically dictate shorter de-oxygenation periods. That is, the incremental benefit of prolonging the de-oxygenation treatment is at some point offset by other considerations. For example, if the reactor feed tank 3 shown in FIG. 1 is used as the catalyst de-oxygenation stage, the residence time of the catalyst slurry in the reactor feed tank may be adjusted by adjusting the volume of the reaction feed mixture in the feed tank relative to the working volume of aqueous reaction mixture within reactor 3. However, since longer residence times in reactor feed tank 3 require a larger catalyst inventory in the reactor system, the benefits of longer residence times must be weighed against the increased catalyst costs, which may become significant, especially in the case of a catalyst comprising a carbon-supported noble metal. Preferably, during catalyst de-oxygenation treatment in reactor feed tank 3, the residence time of the recycled catalyst slurry fraction in the reactor feed tank is at least about 2 minutes, more preferably at least about 4 minutes, even more preferably from about 4 to about 40 minutes. In the case of an oxidation reactor system operated in a batch or semi-batch mode, the residence time of the catalyst slurry fraction in the catalyst recycle tank used as the de-oxygenation stage is typically at least about 5 to about 15 minutes or longer. In such applications, the de-oxygenation treatment is preferably conducted in the catalyst recycle tank for substantially the entire time the catalyst is present in the tank.

De-oxygenation of the noble metal on carbon catalyst may be indirectly monitored by measuring the dissolved molecular oxygen content of the liquid medium in contact with the catalyst particles during the de-oxygenation treatment using a conventional oxygen concentration probe immersed in the liquid medium. A suitable oxygen concentration probe is commercially available from Ocean Optics, Dunedin, Fla., USA. Preferably, the de-oxygenation treatment is carried out in a manner and for a time sufficient to reduce the dissolved oxygen concentration of the catalyst slurry to no greater than 5 ppm, more preferably, no greater than about 3 ppm, even more preferably no greater than about 1 ppm and especially no greater than about 0.5 ppm.

As described above, the non-oxidizing environment to which the catalyst slurry is exposed during the de-oxygenation treatment may consist essentially of a non-oxidizing gas. In accordance with a further embodiment of the present invention, the non-oxidizing environment may comprise a mixture of a non-oxidizing gas and a reducing gas. In a still further alternative embodiment, the non-oxidizing environment consists essentially of a reducing gas. Suitable reducing gases include hydrogen ($H_2$) and carbon monoxide (CO) and mixtures thereof (e.g., synthesis gas). Exposing the noble metal on carbon catalyst to a non-oxidizing environment comprising a reducing gas has the same effect as a non-oxidizing gas with respect to dislodging and removing molecular oxygen adsorbed or otherwise entrapped in the catalyst structure. Exposure to a reducing gas provides the additional benefit of reducing oxidized noble metal to catalytically active and less soluble elemental form, thereby reinvigorating the formaldehyde and formic acid oxidation activity of the catalyst and extending its useful life. The de-oxygenation stage when used to expose the noble metal on carbon catalyst to a non-oxidizing environment comprising a reducing gas is operated in essentially the same manner as previously described. However, it may be necessary to employ a more rigorous vapor recovery system for the resulting mixture of reducing gas, oxygen and other purged components of the catalyst slurry. In accordance with an especially preferred embodiment, the non-oxidizing environment consists essentially of hydrogen. When hydrogen is used in the catalyst de-oxygenation stage, precautions should be taken to minimize the safety risk associated with mixtures of hydrogen and oxygen. For example, it is preferred to first remove substantially all of the dissolved oxygen content from the catalyst slurry using a non-oxidizing gas such as nitrogen before introducing hydrogen into the catalyst slurry and, once treatment with the hydrogen gas is completed, to then scavenge dissolved hydrogen from the catalyst slurry, again using nitrogen or other non-oxidizing gas. De-oxygenation treatment of the catalyst slurry using a reducing gas may be in addition to other reduction treatments intended to reduce the surface of the catalyst after it has become oxidized, for example by contacting the catalyst with other reducing agents (e.g., formaldehyde and/or formic acid in various recycle streams obtained from concentration and purification of the N-(phosphonomethyl)glycine product) introduced continuously or intermittently into the reactor system as disclosed by Ebner et al., U.S. Pat. No. 6,417,133 and Haupfear et al., U.S. Published Application No. US 2002/0068836 A1.

In a still further embodiment of the present invention, the noble metal on carbon catalyst may be exposed to a non-oxidizing environment by subjecting the catalyst slurry to sub-atmospheric pressure (i.e., a vacuum). For example, reactor feed tank 3 or catalyst recycle tank 25 in FIG. 1 could be maintained at sub-atmospheric pressure sufficiently low to remove dissolved oxygen from the catalyst slurry. However, given the increased complexity and operational costs associated with a vacuum catalyst de-oxygenation stage and associated vapor recovery system, it is preferred to provide a suitably non-oxidizing environment by introducing a non-oxidizing and/or reducing gas into the de-oxygenation stage as described above.

The following examples are simply intended to further illustrate and explain the present invention. This invention, therefore, should not be limited to any of the details in these examples.

EXAMPLE 1

An experiment was conducted to determine the effect of nitrogen sparging on dissolved oxygen levels in aqueous systems. Deionized water (300 mL) at 80° C. was placed in a round-bottom flask provided with a magnetic stirrer. Nitrogen gas at 200 $cm^3$/min was sparged into the stirred deionized water at atmospheric pressure through a subsurface dip tube. Dissolved oxygen concentration in the deionized water, in ppm, was measured during nitrogen sparging using a detection apparatus from Ocean Optics, Dunedin, Fla., USA (LS-450 blue LED light source connected to a fibre-optic cable with a ⅛ inch (3.2 mm) OD 10 inch (25.4 cm) long stainless steel probe and an Ocean Optics S2000-FL spectrometer). Results are reported in Table 1 below.

TABLE 1

| Time (min) | ppm $O_2$ | Time (min) | ppm $O_2$ | Time (min) | ppm $O_2$ |
|---|---|---|---|---|---|
| 0.1 | 2.03 | 3.5 | 2.49 | 7.0 | 1.71 |
| 0.5 | 2.13 | 4.0 | 2.51 | 7.5 | 0.98 |
| 1.0 | 2.27 | 4.5 | 2.52 | 8.0 | 0.52 |
| 1.5 | 2.37 | 5.0 | 2.55 | 8.5 | 0.19 |
| 2.0 | 2.46 | 5.5 | 2.53 | 9.0 | 0.0 |
| 2.5 | 2.42 | 6.0 | 2.56 | — | — |
| 3.0 | 2.46 | 6.5 | 2.82 | — | — |

EXAMPLE 2

An experiment was conducted to determine the effect of nitrogen sparging on dissolved oxygen levels in an aqueous catalyst slurry comprising a noble metal on carbon catalyst. The catalyst had previously been used in about 490 batch oxidation reactions in which N-(phosphonomethyl) iminodiacetic acid was oxidized to N-(phosphonomethyl) glycine and originally contained about 5% by weight platinum and about 0.5% by weight iron on an activated particulate carbon support. The used catalyst (6.25 g) was slurried in about 300 mL of water in a pressure vessel provided with a stirrer. Oxygen was sparged into the stirred catalyst slurry at about 80° C. through a subsurface dip tube until the pressure in the vessel reached about 15 psig. The pressure was maintained at 15 psig for about 5 minutes. Thereafter, the stirred slurry was sparged at atmospheric pressure with a flow of 200 $cm^3$/min of nitrogen. Dissolved oxygen concentration in the slurry was measured during nitrogen sparging using the Ocean Optics detection apparatus described above. Results are reported in Table 2 below.

TABLE 2

| Time (min) | ppm $O_2$ | Time (min) | ppm $O_2$ | Time (min) | ppm $O_2$ |
|---|---|---|---|---|---|
| 0.1 | 4.51 | 4.5 | 1.19 | 9.0 | 0.38 |
| 0.5 | 4.17 | 5.0 | 0.66 | 9.5 | 0.36 |

TABLE 2-continued

| Time (min) | ppm O$_2$ | Time (min) | ppm O$_2$ | Time (min) | ppm O$_2$ |
|---|---|---|---|---|---|
| 1.0 | 3.84 | 5.5 | 0.51 | 10.0 | 0.35 |
| 1.5 | 3.55 | 6.0 | 0.48 | 10.5 | 0.34 |
| 2.0 | 3.28 | 6.5 | 0.46 | 11.0 | 0.33 |
| 2.5 | 2.98 | 7.0 | 0.45 | 11.5 | 0.27 |
| 3.0 | 2.74 | 7.5 | 0.43 | 12.0 | 0.23 |
| 3.5 | 2.52 | 8.0 | 0.42 | 12.5 | 0.22 |
| 4.0 | 2.35 | 8.5 | 0.40 | 13.0 | 0.21 |

EXAMPLE 3

Three series of batch N-(phosphonomethyl)iminodiacetic acid oxidation reactions were carried out to determine if a catalyst de-oxygenation treatment including nitrogen sparging of an isolated noble metal on carbon catalyst slurry between oxidation batches improved catalyst performance.

The oxidation reactions were conducted in a 1 liter autoclave (Engineers Autoclave) fitted with an agitator having an impeller located near the bottom of the autoclave. A subsurface dip tube fitted with a 1 inch fritted bayonet-type end situated just below the impeller was provided for introducing oxygen and nitrogen gases into the autoclave. The autoclave had an internal catalyst filter for separating the noble metal on carbon catalyst from the N-(phosphonomethyl)glycine product fraction withdrawn from the autoclave at the conclusion of the oxidation reaction.

Each reaction series included twenty (20) N-(phosphonomethyl)iminodiacetic acid batch oxidation reactions reusing the same catalyst charge. For the first oxidation reaction in each series, 6.25 g of fresh Degussa DB-25 bifunctional oxidation catalyst comprising 5% by weight platinum and 0.48% by weight iron on a particulate carbon support, 60.5 g of N-(phosphonomethyl)iminodiacetic acid and make-up solution to 500 g total reaction mass (1.25% catalyst loading) were charged to the autoclave. The make-up solution contained 0.1% formaldehyde and 0.5% formic acid. Fresh catalyst from the same manufacturer's lot was used at the start of each reaction series. The impeller speed was set at 1000 rpm. At zero time, 392 cm$^3$/min of oxygen was introduced through the dip tube into the agitated aqueous reaction mixture at 100° C. and 110 psig. After about 28 minutes, the oxygen flow was dropped to 125 cm$^3$/min and held at that rate for about 5 minutes past the point where the N-(phosphonomethyl)iminodiacetic acid was depleted. The noble metal on carbon oxidation catalyst was then separated from the reaction product mixture containing N-(phosphonomethyl)glycine to form an isolated catalyst slurry fraction and a product fraction. The isolated catalyst was then used in the next oxidation reaction in the series. This process was repeated for each reaction such that the initial catalyst charge was recovered and reused for each of the subsequent 19 oxidation batch reactions in the series.

In reaction series 1, the catalyst slurry isolated after each oxidation reaction run was not subjected to a de-oxygenation treatment. In reaction series 2 and 3, the isolated catalyst slurry was subjected to a de-oxygenation treatment between every oxidation reaction run. The de-oxygenation treatment included adding about 200 mL of water to the filtered catalyst retained in the autoclave and sparging nitrogen into the resulting catalyst slurry through the dip tube while stirring for 15 minutes at a pressure of 15 psig. In reaction series 2, the nitrogen flow rate was 200 cm$^3$/min. In reaction series 3, the nitrogen flow rate was 26 cm$^3$/min.

The reaction product fraction from each reaction was analyzed by high pressure liquid chromatography (HPLC) to determine the composition with respect to the following: N-(phosphonomethyl)glycine (glyphosate), formaldehyde (CH2O), formic acid (HCO2H), N-(phosphonomethyl)iminodiacetic acid (PMIDA), aminomethylphosphonic acid (AMPA)+N-methylaminomethylphosphonic acid (MAMPA), imino-bis-(methylene)-bis-phosphonic acid (iminobis), N-methyl-N-(phosphonomethyl)glycine (NMG), phosphate (PO4) and N-formylglyphosate (NFG). The results are reported in Tables 3a–c below. Concentrations are in percent by weight. N.D. indicates "Not Detected."

TABLE 3a

Reaction Series 1 - No Catalyst De-oxygenation Treatment

| Reaction # | 1 | 2 | 3 | 4 | 5 | 6 | 7 |
|---|---|---|---|---|---|---|---|
| % glyphosate | 7.86 | 8.20 | 7.99 | 8.64 | 8.31 | 8.35 | 8.21 |
| % CH$_2$O | 0.024 | 0.018 | 0.016 | 0.017 | 0.017 | 0.019 | 0.017 |
| % HCO$_2$H | 0.172 | 0.187 | 0.185 | 0.206 | 0.216 | 0.202 | 0.182 |
| % PMIDA | N.D. | N.D. | N.D. | N.D. | N.D. | N.D. | 0.009 |
| % AMPA + % MAMPA | 0.159 | 0.152 | 0.147 | 0.063 | 0.133 | 0.143 | 0.137 |
| % iminobis | 0.062 | 0.065 | 0.080 | 0.057 | 0.069 | 0.088 | 0.094 |
| % NMG | 0.009 | N.D. | N.D. | 0.007 | 0.004 | N.D. | N.D. |
| % PO$_4$ | 0.199 | 0.082 | 0.066 | 0.053 | 0.055 | 0.070 | 0.199 |
| % NFG | 0.179 | 0.152 | 0.158 | 0.151 | 0.166 | 0.136 | 0.150 |

| Reaction # | 8 | 9 | 10 | 11 | 12 | 13 | 14 |
|---|---|---|---|---|---|---|---|
| % glyphosate | 8.28 | 8.30 | 8.34 | 8.24 | 8.32 | 8.33 | 8.27 |
| % CH$_2$O | 0.015 | 0.014 | 0.015 | 0.018 | 0.019 | 0.018 | 0.020 |
| % HCO$_2$H | 0.194 | 0.194 | 0.201 | 0.218 | 0.243 | 0.244 | 0.267 |
| % PMIDA | 0.010 | 0.008 | N.D. | 0.007 | 0.010 | 0.012 | 0.008 |
| % AMPA + % MAMPA | 0.137 | 0.106 | 0.122 | 0.110 | 0.127 | 0.130 | 0.113 |
| % iminobis | 0.096 | 0.088 | 0.087 | 0.090 | 0.100 | 0.103 | 0.096 |
| % NMG | N.D. | N.D. | N.D. | N.D. | N.D. | N.D. | N.D. |
| % PO$_4$ | 0.102 | 0.090 | 0.075 | 0.081 | 0.077 | 0.072 | 0.064 |
| % NFG | 0.147 | 0.141 | 0.149 | 0.174 | 0.167 | 0.182 | 0.184 |

| Reaction # | 15 | 16 | 17 | 18 | 19 | 20 |
|---|---|---|---|---|---|---|
| % glyphosate | 8.31 | 8.35 | 8.25 | 8.28 | 8.30 | 8.26 |
| % CH$_2$O | 0.015 | 0.018 | 0.020 | 0.024 | 0.021 | 0.019 |
| % HCO$_2$H | 0.243 | 0.266 | 0.259 | 0.281 | 0.274 | 0.246 |
| % PMIDA | N.D. | N.D. | N.D. | N.D. | N.D. | N.D. |
| % AMPA + % MAMPA | 0.102 | 0.101 | 0.090 | 0.100 | 0.093 | 0.098 |
| % iminobis | 0.071 | 0.069 | 0.070 | 0.069 | 0.070 | 0.069 |
| % NMG | N.D. | N.D. | N.D. | N.D. | N.D. | N.D. |
| % PO$_4$ | 0.045 | 0.042 | 0.046 | 0.041 | 0.040 | 0.041 |
| % NFG | 0.163 | 0.176 | 0.162 | 0.186 | 0.179 | 0.157 |

TABLE 3b

Reaction Series 2 - Catalyst De-oxygenation Treatment with 200 cm$^3$/min Nitrogen Sparge

| Reaction # | 1 | 2 | 3 | 4 | 5 | 6 | 7 |
|---|---|---|---|---|---|---|---|
| % glyphosate | 7.89 | 8.18 | 8.29 | 8.41 | 8.34 | 8.34 | 8.27 |
| % CH$_2$O | 0.021 | 0.015 | 0.016 | 0.013 | 0.012 | 0.015 | 0.016 |
| % HCO$_2$H | 0.164 | 0.171 | 0.191 | 0.212 | 0.184 | 0.183 | 0.192 |
| % PMIDA | N.D. | N.D. | N.D. | N.D. | N.D. | N.D. | 0.006 |
| % AMPA + % MAMPA | 0.143 | 0.127 | 0.123 | 0.101 | 0.099 | 0.110 | 0.094 |
| % iminobis | 0.062 | 0.066 | 0.070 | 0.063 | 0.069 | 0.070 | 0.070 |
| % NMG | N.D. | N.D. | N.D. | N.D. | N.D. | N.D. | N.D. |
| % PO$_4$ | 0.204 | 0.081 | 0.062 | 0.049 | 0.059 | 0.053 | 0.055 |
| % NFG | 0.007 | 0.006 | 0.005 | 0.005 | 0.005 | 0.147 | 0.143 |

TABLE 3b-continued

| Reaction # | 8 | 9 | 10 | 11 | 12 | 13 | 14 |
|---|---|---|---|---|---|---|---|
| % glyphosate | 8.27 | 8.26 | 8.24 | 8.41 | 8.43 | 8.28 | 8.31 |
| % $CH_2O$ | 0.019 | 0.018 | 0.018 | 0.016 | 0.017 | 0.014 | 0.014 |
| % $HCO_2H$ | 0.192 | 0.192 | 0.193 | 0.206 | 0.244 | 0.231 | 0.228 |
| % PMIDA | 0.007 | 0.006 | N.D. | 0.006 | 0.011 | 0.007 | 0.008 |
| % AMPA + % MAMPA | 0.110 | 0.106 | 0.118 | 0.079 | 0.089 | 0.077 | 0.083 |
| % iminobis | 0.070 | 0.069 | 0.069 | 0.070 | 0.069 | 0.069 | 0.068 |
| % NMG | N.D. | N.D. | N.D. | N.D. | N.D. | N.D. | N.D. |
| % $PO_4$ | 0.051 | 0.051 | 0.048 | 0.049 | 0.044 | 0.048 | 0.046 |
| % NFG | 0.145 | 0.143 | 0.143 | 0.148 | 0.164 | 0.154 | 0.154 |

| Reaction # | 15 | 16 | 17 | 18 | 19 | 20 |
|---|---|---|---|---|---|---|
| % Glyphosate | 8.35 | 8.40 | 8.32 | 8.24 | 8.30 | 8.24 |
| % $CH_2O$ | 0.013 | 0.017 | 0.013 | 0.012 | 0.013 | 0.012 |
| % $HCO_2H$ | 0.213 | 0.252 | 0.237 | 0.235 | 0.241 | 0.245 |
| % PMIDA | N.D. | N.D. | N.D. | N.D. | N.D. | N.D. |
| % AMPA + % MAMPA | 0.095 | 0.088 | 0.082 | 0.080 | 0.084 | 0.079 |
| % Iminobis | 0.068 | 0.068 | 0.067 | 0.069 | 0.068 | 0.068 |
| % NMG | N.D. | N.D. | N.D. | N.D. | N.D. | N.D. |
| % $PO_4$ | 0.045 | 0.046 | 0.050 | 0.049 | 0.048 | 0.046 |
| % NFG | 0.142 | 0.162 | 0.163 | 0.148 | 0.150 | 0.149 |

TABLE 3c

Reaction Series 3 - Catalyst De-oxygenation Treatment with 26 $cm^3$/min Nitrogen Sparge

| Reaction # | 1 | 2 | 3 | 4 | 5 | 6 | 7 |
|---|---|---|---|---|---|---|---|
| % glyphosate | 7.94 | 8.09 | 8.16 | 8.32 | 8.29 | 8.30 | 8.18 |
| % $CH_2O$ | 0.016 | 0.010 | 0.009 | 0.010 | 0.010 | 0.010 | 0.011 |
| % $HCO_2H$ | 0.166 | 0.154 | 0.160 | 0.162 | 0.172 | 0.189 | 0.192 |
| % PMIDA | N.D. | N.D. | N.D. | N.D. | N.D. | N.D. | 0.008 |
| % AMPA + % MAMPA | 0.120 | 0.126 | 0.111 | 0.090 | 0.096 | 0.100 | 0.100 |
| % iminobis | 0.058 | 0.065 | 0.067 | 0.061 | 0.060 | 0.063 | 0.063 |
| % NMG | N.D. | N.D. | N.D. | N.D. | N.D. | N.D. | N.D. |
| % $PO_4$ | 0.190 | 0.100 | 0.085 | 0.071 | 0.063 | 0.063 | 0.063 |
| % NFG | 0.203 | 0.150 | 0.143 | 0.145 | 0.144 | 0.160 | 0.153 |

| Reaction # | 8 | 9 | 10 | 11 | 12 | 13 | 14 |
|---|---|---|---|---|---|---|---|
| % glyphosate | 8.28 | 8.15 | 8.17 | 8.29 | 8.36 | 8.50 | 8.32 |
| % $CH_2O$ | 0.010 | 0.010 | 0.010 | 0.012 | 0.011 | 0.014 | 0.013 |
| % $HCO_2H$ | 0.194 | 0.211 | 0.189 | 0.226 | 0.226 | 0.223 | 0.223 |
| % PMIDA | 0.009 | 0.008 | N.D. | 0.011 | 0.010 | 0.013 | N.D. |
| % AMPA + % MAMPA | 0.087 | 0.082 | 0.086 | 0.082 | 0.077 | 0.116 | 0.097 |
| % iminobis | 0.062 | 0.060 | 0.061 | 0.069 | 0.068 | 0.071 | 0.068 |
| % NMG | N.D. | N.D. | N.D. | N.D. | N.D. | N.D. | N.D. |
| % $PO_4$ | 0.058 | 0.055 | 0.054 | 0.063 | 0.064 | 0.063 | 0.059 |
| % NFG | 0.136 | 0.135 | 0.150 | 0.163 | 0.145 | 0.163 | 0.158 |

| Reaction # | 15 | 16 | 17 | 18 | 19 | 20 |
|---|---|---|---|---|---|---|
| % glyphosate | 8.22 | 8.26 | 8.30 | 8.22 | 8.28 | 8.26 |
| % $CH_2O$ | 0.013 | 0.015 | 0.016 | 0.017 | 0.015 | 0.012 |
| % $HCO_2H$ | 0.220 | 0.234 | 0.231 | 0.235 | 0.224 | 0.199 |
| % PMIDA | N.D. | N.D. | N.D. | N.D. | N.D. | N.D. |
| % AMPA + % MAMPA | 0.090 | 0.092 | 0.097 | 0.098 | 0.091 | 0.070 |
| % iminobis | 0.064 | 0.065 | 0.068 | 0.068 | 0.067 | 0.059 |
| % NMG | N.D. | N.D. | N.D. | N.D. | N.D. | N.D. |
| % $PO_4$ | 0.052 | 0.050 | 0.068 | 0.068 | 0.067 | 0.059 |
| % NFG | 0.152 | 0.149 | 0.167 | 0.151 | 0.183 | 0.158 |

Averages for glyphosate, formaldehyde and formic acid concentrations in the reaction product fractions for each reaction series are reported in Tables 3d and 3e below and the data is compared versus reaction series 1 without the de-oxygenation treatment.

TABLE 3d

Overall Averages - Oxidation Reactions 1–20

| Reaction Series | 1 | 2 | % change v. rx. series 1 | 3 | % change v. rx. series 1 |
|---|---|---|---|---|---|
| % glyphosate | 8.27 | 8.29 | +0.24 | 8.24 | −0.36 |
| % $CH_2O$ | 0.018 | 0.015 | −16.7 | 0.012 | −50.0 |
| % $HCO_2H$ | 0.224 | 0.210 | −6.25 | 0.201 | −10.3 |

TABLE 3e

Overall Averages - Oxidation Reactions 11–20

| Reaction Series | 1 | 2 | % change v. rx. series 1 | 3 | % change v. rx. series 1 |
|---|---|---|---|---|---|
| % glyphosate | 8.29 | 8.33 | +0.46 | 8.30 | +0.12 |
| % $CH_2O$ | 0.019 | 0.014 | −26.3 | 0.014 | −26.3 |
| % $HCO_2H$ | 0.254 | 0.233 | −8.27 | 0.224 | −11.8 |

The data show that the de-oxygenation treatment of the isolated catalyst slurry by introducing nitrogen at either 200 $cm^3$/min or 26 $cm^3$/min produces reaction product mixtures of higher purity as compared to reaction series 1 which did not include a catalyst de-oxygenation treatment. In particular, the de-oxygenated catalyst gave reduced levels of the $C_1$ reaction by-products, formaldehyde and formic acid. As indicated by a comparison of the overall averages for oxidation reactions 1–20 and 11–20, the benefits of the de-oxygenation treatment generally remained constant over the number of oxidation reactions evaluated.

EXAMPLE 4

Five series of batch N-(phosphonomethyl)iminodiacetic acid oxidation reactions were conducted using the experimental apparatus described in Example 3 to determine if a de-oxygenation treatment including hydrogen or nitrogen sparging of an isolated noble metal on carbon catalyst slurry between oxidation batches improved catalyst performance.

For the first oxidation reaction of each series, 2.5 g of fresh Degussa DB-20 bifunctional oxidation catalyst comprising 5% by weight platinum and 0.65% by weight iron on a particulate carbon support, 60.5 g of N-(phosphonomethyl)iminodiacetic acid substrate and make-up solution to 500 g total reaction mass (0.5% catalyst loading) were charged to the autoclave. The make-up solution contained 0.1% formaldehyde and 0.5% formic acid. Fresh catalyst from the same manufacturer's lot was used at the start of each reaction series. The impeller speed was set at 1000 rpm. At zero time, a flow of 335 $cm^3$/min of oxygen was introduced through the dip tube into the aqueous reaction mixture at 100° C. and 110 psig. At the end of the oxidation reaction, the noble metal on carbon oxidation catalyst was then separated from the reaction product mixture containing N-(phosphonomethyl)glycine to form an isolated catalyst slurry fraction and a product fraction. The isolated catalyst was then used in the next oxidation reaction in the series. This process was repeated for each reaction such that the initial catalyst charge was recovered and reused for each of the subsequent batch oxidation reactions in the series. In those series including a catalyst de-oxygenation treatment, about 200 mL of water was added to the filtered catalyst retained in the autoclave and the resulting catalyst slurry subjected to the de-oxygenation treatment.

The reaction product fraction from each reaction was analyzed by HPLC to determine the composition with respect to the following: glyphosate, formaldehyde, formic acid, PMIDA, AMPA+MAMPA, iminobis, NMG, PO$_4$, NFG, iminodiacetic acid (IDA), AMPA and glycine.

In reaction series 1, the catalyst slurry isolated after each oxidation reaction run was not subjected to a de-oxygenation treatment. Results are reported in Table 4a below.

TABLE 4a

Reaction Series 1 - Without De-oxygenation Treatment

| Reaction # | 1 | 2 | 3 | 4 | 5 | 6 | 7 | 8 |
|---|---|---|---|---|---|---|---|---|
| % glyphosate | 8.22 | 8.19 | 7.93 | 8.10 | 8.01 | 8.08 | 7.97 | 8.02 |
| % CH$_2$O | 0.077 | 0.067 | N.D. | 0.146 | 0.218 | 0.225 | 0.229 | 0.241 |
| % HCO$_2$H | 0.439 | 0.471 | N.D. | 0.729 | 0.806 | 0.924 | 0.927 | 0.922 |
| % PMIDA | 0.020 | 0.038 | 0.031 | 0.048 | 0.067 | 0.045 | 0.093 | 0.057 |
| % AMPA + % MAMPA | 0.067 | 0.063 | 0.143 | 0.071 | 0.089 | 0.080 | 0.088 | 0.087 |
| % iminobis | 0.055 | 0.056 | 0.056 | 0.054 | 0.055 | 0.053 | 0.054 | 0.055 |
| % NMG | 0.013 | 0.015 | 0.005 | 0.067 | 0.098 | 0.147 | 0.163 | 0.167 |
| % PO$_4$ | 0.155 | 0.087 | 0.075 | 0.063 | 0.053 | 0.060 | 0.057 | 0.059 |
| % NFG | 0.209 | 0.202 | 0.213 | 0.262 | 0.268 | 0.313 | 0.314 | 0.356 |
| % IDA | 0.167 | 0.086 | 0.069 | 0.053 | 0.026 | 0.030 | 0.026 | 0.030 |
| % AMPA | 0.046 | 0.039 | 0.084 | 0.033 | 0.033 | 0.037 | 0.038 | 0.036 |

| Reaction # | 9 | 10 | 11 | 12 | 13 | 14 | 15 | 16 |
|---|---|---|---|---|---|---|---|---|
| % glyphosate | 7.97 | 7.91 | 7.89 | 7.81 | 7.98 | 7.94 | 7.99 | 7.88 |
| % CH$_2$O | 0.245 | 0.249 | 0.251 | 0.274 | 0.279 | 0.280 | 0.285 | 0.284 |
| % HCO$_2$H | 0.941 | 0.984 | 0.943 | 0.906 | 0.969 | 1.002 | 0.965 | 0.991 |
| % PMIDA | 0.047 | 0.054 | 0.048 | 0.050 | 0.029 | 0.038 | 0.034 | 0.036 |
| % AMPA + % MAMPA | 0.088 | 0.092 | 0.087 | 0.088 | 0.092 | 0.096 | 0.087 | 0.112 |
| % iminobis | 0.055 | 0.052 | 0.053 | 0.053 | 0.053 | 0.054 | 0.053 | 0.220 |
| % NMG | 0.183 | 0.186 | 0.167 | 0.167 | 0.198 | 0.205 | 0.198 | 0.040 |
| % PO$_4$ | 0.057 | 0.055 | 0.054 | 0.054 | 0.055 | 0.054 | 0.053 | 0.040 |
| % NFG | 0.363 | 0.367 | 0.355 | 0.354 | 0.376 | 0.376 | 0.365 | 0.332 |
| % IDA | 0.025 | 0.027 | 0.026 | 0.025 | 0.023 | 0.021 | 0.022 | 0.021 |
| % AMPA | 0.038 | 0.039 | 0.035 | 0.036 | 0.039 | 0.038 | 0.036 | 0.038 |

In the second reaction series, the isolated catalyst slurry was subjected to a de-oxygenation treatment between every oxidation reaction run. The de-oxygenation treatment included sparging hydrogen at 200 cm$^3$/min into the stirred isolated catalyst slurry at 15 psig for 15 minutes just prior to the next reaction in the series. Results are reported in Table 4b below.

TABLE 4b

Reaction Series 2 - Catalyst De-oxygenation Treatment with 200 cm$^3$/min Hydrogen Sparge

| Reaction # | 1 | 2 | 3 | 4 | 5 | 6 | 7 |
|---|---|---|---|---|---|---|---|
| % glyphosate | 8.12 | 8.25 | 7.23 | 7.87 | 8.14 | 7.93 | 8.17 |
| % CH$_2$O | 0.069 | 0.054 | 0.052 | 0.055 | 0.053 | 0.063 | 0.067 |
| % HCO$_2$H | 0.394 | 0.385 | 0.319 | 0.367 | 0.372 | 0.387 | 0.441 |
| % PMIDA | 0.014 | 0.016 | 0.020 | 0.013 | 0.015 | 0.028 | 0.030 |
| % AMPA + % MAMPA | 0.025 | 0.021 | 0.016 | 0.018 | 0.019 | 0.053 | 0.057 |
| % iminobis | 0.019 | 0.019 | 0.011 | 0.018 | 0.019 | 0.048 | 0.054 |
| % NMG | 0.004 | 0.003 | 0.004 | 0.003 | 0.003 | 0.010 | 0.016 |
| % PO$_4$ | 0.060 | 0.039 | 0.033 | 0.048 | 0.049 | 0.142 | 0.121 |
| % NFG | 0.236 | 0.222 | 0.188 | 0.216 | 0.229 | 0.232 | 0.242 |
| % IDA | 0.067 | 0.045 | 0.041 | 0.053 | 0.058 | 0.164 | 0.136 |
| % AMPA | 0.047 | 0.043 | 0.037 | 0.036 | 0.037 | 0.033 | 0.032 |
| % glycine | 0.015 | 0.013 | 0.012 | 0.014 | 0.015 | 0.014 | 0.014 |

| Reaction # | 8 | 9 | 10 | 11 | 12 | 13 | 14 |
|---|---|---|---|---|---|---|---|
| % glyphosate | 8.24 | 8.23 | 8.26 | 8.24 | 8.29 | 8.18 | 8.29 |
| % CH$_2$O | 0.067 | 0.076 | 0.075 | 0.076 | 0.068 | 0.071 | 0.068 |
| % HCO$_2$H | 0.433 | 0.503 | 0.470 | 0.483 | 0.486 | 0.505 | 0.528 |
| % PMIDA | 0.023 | 0.022 | 0.017 | 0.021 | 0.022 | 0.024 | 0.027 |
| % AMPA + % MAMPA | 0.059 | 0.061 | 0.056 | 0.056 | 0.065 | 0.062 | 0.069 |
| % iminobis | 0.054 | 0.054 | 0.054 | 0.053 | 0.054 | 0.055 | 0.055 |
| % NMG | 0.015 | 0.025 | 0.020 | 0.021 | 0.024 | 0.024 | 0.027 |
| % PO$_4$ | 0.116 | 0.079 | 0.107 | 0.096 | 0.080 | 0.078 | 0.079 |
| % NFG | 0.229 | 0.237 | 0.232 | 0.232 | 0.238 | 0.237 | 0.257 |
| % IDA | 0.132 | 0.085 | 0.120 | 0.107 | 0.086 | 0.085 | 0.090 |
| % AMPA | 0.032 | 0.035 | 0.032 | 0.030 | 0.035 | 0.034 | 0.033 |
| % glycine | 0.013 | 0.013 | 0.013 | 0.013 | 0.013 | 0.013 | 0.013 |

In the third reaction series, the isolated catalyst slurry was subjected to a de-oxygenation treatment between every oxidation reaction run. The de-oxygenation treatment included sparging hydrogen at 50 cm$^3$/min into the stirred isolated catalyst slurry at 15 psig for 15 minutes just prior to the next reaction in the series. Results are reported in Table 4c below.

TABLE 4c

Reaction Series 3 - Catalyst De-oxygenation Treatment with 50 cm$^3$/min Hydrogen Sparge

| Reaction # | 1 | 2 | 3 | 4 | 5 | 6 | 7 |
|---|---|---|---|---|---|---|---|
| % glyphosate | 8.13 | 8.24 | 8.15 | 8.48 | 8.19 | 8.77 | 8.90 |
| % CH$_2$O | 0.084 | 0.081 | 0.136 | 0.070 | 0.060 | 0.077 | 0.080 |
| % HCO$_2$H | 0.431 | 0.450 | 0.561 | 0.450 | 0.402 | 0.515 | 0.508 |
| % PMIDA | 0.018 | 0.013 | 0.029 | 0.018 | 0.040 | 0.019 | 0.043 |
| % AMPA + % MAMPA | 0.081 | 0.081 | 0.112 | 0.083 | 0.064 | 0.067 | 0.058 |
| % iminobis | 0.052 | 0.054 | 0.053 | 0.053 | 0.053 | 0.054 | 0.055 |
| % NMG | 0.015 | 0.016 | 0.023 | 0.019 | 0.012 | 0.026 | 0.027 |
| % PO$_4$ | 0.152 | 0.111 | 0.103 | 0.097 | 0.151 | 0.107 | 0.131 |
| % NFG | 0.235 | 0.244 | 0.251 | 0.249 | 0.244 | 0.279 | 0.278 |
| % IDA | 0.346 | 0.308 | 0.294 | 0.270 | 0.348 | N.D. | N.D. |
| % AMPA | 0.043 | 0.044 | 0.065 | 0.040 | 0.031 | 0.037 | 0.032 |
| % glycine | 0.014 | 0.014 | 0.014 | 0.014 | 0.015 | 0.015 | 0.016 |

| Reaction # | 8 | 9 | 10 | 11 | 12 | 13 | 14 |
|---|---|---|---|---|---|---|---|
| % glyphosate | 8.76 | 8.71 | 8.82 | 8.82 | 8.73 | 8.69 | 8.44 |
| % CH$_2$O | 0.070 | 0.092 | 0.087 | 0.090 | 0.087 | 0.099 | 0.095 |
| % HCO$_2$H | 0.503 | 0.620 | 0.587 | 0.597 | 0.594 | 0.608 | 0.578 |
| % PMIDA | 0.045 | 0.043 | 0.041 | 0.041 | 0.049 | 0.040 | 0.031 |
| % AMPA + % MAMPA | 0.056 | 0.061 | 0.058 | 0.058 | 0.059 | 0.059 | 0.058 |
| % iminobis | 0.054 | 0.055 | 0.054 | 0.054 | 0.055 | 0.054 | 0.053 |
| % NMG | 0.018 | 0.034 | 0.031 | 0.033 | 0.032 | 0.036 | 0.030 |
| % PO$_4$ | 0.148 | 0.109 | 0.120 | 0.118 | 0.119 | 0.114 | 0.132 |
| % NFG | 0.264 | 0.296 | 0.291 | 0.289 | 0.289 | 0.298 | 0.288 |
| % IDA | N.D. | N.D. | 0.129 | 0.122 | N.D. | 0.117 | 0.141 |
| % AMPA | 0.033 | 0.035 | 0.031 | 0.031 | 0.029 | 0.029 | 0.030 |
| % glycine | 0.016 | 0.015 | 0.015 | 0.015 | 0.014 | 0.014 | 0.014 |

| Reaction # | 15 | 16 | 17 | 18 | 19 | 20 |
|---|---|---|---|---|---|---|
| % glyphosate | 8.80 | 7.62 | 7.76 | 7.86 | 7.74 | 7.87 |
| % CH$_2$O | 0.108 | 0.113 | 0.114 | 0.311 | 0.146 | 0.142 |
| % HCO$_2$H | 0.646 | 0.643 | 0.641 | 1.096 | 0.795 | 0.752 |
| % PMIDA | 0.034 | 0.034 | 0.039 | 0.026 | 0.017 | 0.033 |
| % AMPA + % MAMPA | 0.032 | 0.069 | 0.064 | 0.133 | 0.075 | 0.069 |
| % iminobis | 0.028 | 0.053 | 0.053 | 0.052 | 0.052 | 0.053 |
| % NMG | 0.024 | 0.047 | 0.048 | 0.149 | 0.079 | 0.068 |
| % PO$_4$ | 0.058 | 0.104 | 0.113 | 0.056 | 0.083 | 0.095 |
| % NFG | 0.323 | 0.296 | 0.297 | 0.393 | 0.339 | 0.326 |
| % IDA | 0.111 | 0.096 | 0.116 | 0.035 | 0.072 | 0.082 |
| % AMPA | 0.029 | 0.033 | 0.023 | 0.052 | 0.033 | 0.031 |
| % glycine | 0.014 | 0.016 | 0.016 | 0.015 | 0.016 | 0.016 |

In the fourth reaction series, the isolated catalyst slurry was subjected to a de-oxygenation treatment between every oxidation reaction run. The de-oxygenation treatment included sparging nitrogen at 200 cm$^3$/min into the stirred isolated catalyst slurry at 15 psig for 14 minutes just prior to the next reaction in the series. Results are reported in Table 4d below.

TABLE 4d

Reaction Series 4 - Catalyst De-oxygenation Treatment with 200 cm³/min Nitrogen Sparge

| Reaction # | 1 | 2 | 3 | 4 | 5 | 6 |
|---|---|---|---|---|---|---|
| % glyphosate | 8.31 | 8.38 | 8.23 | 8.33 | 8.37 | 8.38 |
| % $CH_2O$ | 0.074 | 0.061 | 0.073 | 0.085 | 0.083 | 0.085 |
| % $HCO_2H$ | 0.422 | 0.424 | 0.431 | N.D. | 0.476 | 0.465 |
| % AMPA + % MAMPA | 0.062 | 0.055 | 0.053 | 0.052 | 0.055 | 0.057 |
| % iminobis | 0.049 | 0.055 | 0.051 | 0.050 | 0.052 | 0.051 |
| % NMG | 0.012 | 0.012 | 0.011 | 0.021 | 0.022 | 0.017 |
| % $PO_4$ | 0.188 | 0.144 | 0.147 | 0.124 | 0.121 | 0.137 |
| % NFG | 0.253 | 0.252 | 0.243 | 0.289 | 0.279 | 0.274 |
| Reaction # | 7 | 8 | 9 | 10 | 11 | 12 |
| % glyphosate | 8.41 | 8.30 | 8.53 | 8.30 | 8.29 | 8.15 |
| % $CH_2O$ | 0.103 | 0.093 | 0.100 | 0.157 | 0.110 | 0.105 |
| % $HCO_2H$ | 0.561 | 0.523 | 0.540 | 0.734 | 0.580 | 0.557 |
| % AMPA + % MAMPA | 0.065 | 0.055 | 0.055 | 0.088 | 0.058 | 0.062 |
| % iminobis | 0.051 | 0.052 | 0.052 | 0.051 | 0.051 | 0.051 |
| % NMG | 0.033 | 0.026 | 0.029 | 0.055 | 0.036 | 0.037 |
| % $PO_4$ | 0.092 | 0.119 | 0.111 | 0.086 | 0.091 | 0.097 |
| % NFG | 0.298 | 0.286 | 0.294 | 0.327 | 0.298 | 0.292 |

In the fifth reaction series, the isolated catalyst slurry was subjected to a de-oxygenation treatment after every fifth oxidation reaction run. The de-oxygenation treatment included sparging hydrogen at 50 cm³/min into the stirred isolated catalyst slurry at 15 psig for 15 minutes. Results are reported in Table 4e below.

TABLE 4e

Reaction Series 5 - Catalyst De-oxygenation Treatment with 50 cm³/min After Every Fifth Reaction

| Reaction # | 1 | 2 | 3 | 4 | 5 | 6 |
|---|---|---|---|---|---|---|
| % glyphosate | 8.23 | 8.14 | 8.15 | 8.31 | 8.32 | 8.16 |
| % $CH_2O$ | 0.093 | 0.080 | 0.093 | 0.101 | 0.111 | 0.224 |
| % $HCO_2H$ | 0.458 | 0.456 | 0.516 | 0.555 | 0.578 | 0.637 |
| % PMIDA | 0.274 | 0.067 | 0.042 | 0.051 | 0.040 | 0.166 |
| % AMPA + % MAMPA | 0.019 | 0.025 | 0.055 | 0.053 | 0.059 | 0.048 |
| % iminobis | 0.034 | 0.037 | 0.051 | 0.055 | 0.054 | 0.051 |
| % NMG | 0.033 | 0.040 | 0.017 | 0.055 | 0.063 | 0.061 |
| % $PO_4$ | 0.011 | 0.012 | 0.156 | 0.076 | 0.061 | 0.080 |
| % NFG | 0.048 | 0.261 | 0.276 | 0.006 | 0.006 | 0.005 |
| % IDA | 0.337 | 0.333 | 0.303 | 0.095 | 0.075 | 0.078 |
| % AMPA | 0.035 | 0.031 | 0.031 | 0.030 | 0.32 | 0.024 |
| % glycine | 0.014 | 0.015 | 0.014 | 0.013 | 0.013 | 0.012 |
| Reaction # | 7 | 8 | 9 | 10 | 11 | 12 |
| % glyphosate | 8.080 | 8.090 | 8.000 | 8.040 | 8.130 | 8.490 |
| % $CH_2O$ | 0.208 | 0.225 | 0.238 | 0.269 | 0.213 | 0.287 |
| % $HCO_2H$ | 0.680 | 0.699 | 0.708 | 0.742 | 0.769 | 0.754 |
| % PMIDA | 0.038 | 0.037 | 0.031 | 0.039 | 0.026 | 0.035 |
| % AMPA + % MAMPA | 0.071 | 0.079 | 0.079 | 0.078 | 0.069 | 0.061 |
| % iminobis | 0.052 | 0.051 | 0.052 | 0.052 | 0.053 | 0.054 |
| % NMG | 0.157 | 0.123 | 0.140 | 0.154 | 0.125 | 0.120 |
| % $PO_4$ | 0.068 | 0.057 | 0.053 | 0.047 | 0.071 | 0.050 |
| % NFG | 0.007 | 0.007 | 0.007 | 0.007 | 0.006 | 0.006 |
| % IDA | 0.070 | 0.058 | 0.054 | 0.050 | 0.081 | 0.047 |
| % AMPA | 0.033 | 0.035 | 0.034 | 0.032 | 0.033 | 0.030 |
| % glycine | 0.017 | 0.016 | 0.015 | 0.015 | 0.016 | 0.015 |

Averages for glyphosate, formaldehyde and formic acid concentrations in the reaction product fraction for each reaction series are reported in Table 4f below and the data is compared versus reaction series 1 without the catalyst de-oxygenation treatment.

TABLE 4f

Overall Averages

| Reaction Series | 1 | 2 | % change v. rx. series 1 | 3 | % change v. rx. series 1 |
|---|---|---|---|---|---|
| % glyphosate | 7.993 | 8.102 | +1.4 | 8.374 | +4.8 |
| % $CH_2O$ | 0.233 | 0.064 | −72.5 | 0.107 | −54.1 |
| % $HCO_2H$ | 0.861 | 0.424 | −50.8 | 0.599 | −30.4 |

| Reaction Series | — | 4 | % change v. rx. series 1 | 5 | % change v. rx. series 1 |
|---|---|---|---|---|---|
| % glyphosate | — | 8.333 | +4.3 | 8.179 | +2.3 |
| % $CH_2O$ | — | 0.094 | −59.7 | 0.179 | −23.2 |
| % $HCO_2H$ | — | 0.519 | −39.7 | 0.629 | −26.9 |

The data in Table 4f indicate that catalyst de-oxygenation by both hydrogen and nitrogen sparging of isolated catalyst slurries gave reduced levels of the $C_1$ reaction by-products, formaldehyde and formic acid. Moreover, the de-oxygenated catalyst produced higher purity glyphosate as indicated by reduced by-product level.

Some of the reaction product fractions from reaction series 1, 2, 3 and 4 were analyzed for platinum content using Inductively Coupled Argon Plasma—Mass Spectroscopy (ICAP-MS). Platinum concentration in ppm is reported in Table 4g below.

TABLE 4g

Product Fraction Platinum Content

| Oxidation Reaction # | 1 | 2 | 6 | 10 | 12 | 15 | 20 |
|---|---|---|---|---|---|---|---|
| Rx series 1 | 0.07 | 0.07 | 0.13 | 0.13 | 0.12 | 0.15 | 0.16 |
| Rx series 2 (200 cc/min $H_2$) | 0.08 | 0.09 | 0.08 | 0.09 | 0.09 | 0.09 | — |
| Rx series 3 (50 cc/min $H_2$) | 0.06 | — | 0.10 | 0.09 | 0.10 | 0.11 | 0.12 |
| Rx series 4 (200 cc/min $N_2$) | — | 0.08 | 0.08 | 0.09 | 0.08 | — | — |

The data in Table 4g indicate that de-oxygenation treatment of the isolated catalyst slurry reduces platinum losses by a factor of about 25%.

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), Applicant notes that unless the context requires otherwise, those words are used on the basis and clear understanding that they are to be interpreted inclusively, rather than exclusively, and that Applicant intends each of those words to be so interpreted in construing this entire specification.

What is claimed is:

1. A process for oxidizing a reagent, the process comprising:

contacting an aqueous reaction mixture comprising the reagent and a heterogenous oxidation catalyst with an oxygen-containing gas in an oxidation reaction zone to oxidize the reagent and produce an aqueous reaction product mixture comprising the oxidized reagent and the oxidation catalyst and having oxygen dissolved therein, the oxidation catalyst comprising a noble metal deposited on a carbon support;

separating at least a portion of the oxidized reagent from the reaction product mixture to form a product fraction comprising the separated oxidized reagent substantially free of the oxidation catalyst and a catalyst slurry fraction comprising the oxidation catalyst in contact with a liquid medium having oxygen dissolved therein;

subjecting the catalyst slurry fraction to a de-oxygenation treatment to reduce the dissolved oxygen concentration in the catalyst slurry fraction; and recycling and introducing the de-oxygenated catalyst slurry fraction into the oxidation reaction zone.

2. A process as set forth in claim 1 wherein the reagent is selected from the group consisting of N-(phosphonomethyl)iminodiacetic acid substrates, N-substituted-N-(phosphonomethyl)glycine substrates, formaldehyde, formic acid and mixtures thereof.

3. A process as set forth in claim 1 wherein the reagent is an N-(phosphonomethyl)iminodiacetic acid substrate and the reaction product mixture comprises an N-(phosphonomethyl)glycine product.

4. A process as set forth in claim 1 wherein the de-oxygenation treatment comprises exposing the catalyst slurry fraction to a non-oxidizing environment.

5. A process as set forth in claim 4 wherein the non-oxidizing environment comprises a non-oxidizing gas.

6. A process as set forth in claim 5 wherein the non-oxidizing gas is selected from the group consisting of nitrogen, argon, helium and mixtures thereof.

7. A process as set forth in claim 4 wherein the non-oxidizing environment comprises a mixture of a non-oxidizing gas and a reducing gas.

8. A process as set forth in claim 7 wherein the reducing gas is selected from the group consisting of hydrogen, carbon monoxide and mixtures thereof.

9. A process as set forth in claim 4 wherein the non-oxidizing environment consists essentially of a reducing gas.

10. A process as set forth in claim 9 wherein the reducing gas is selected from the group consisting of hydrogen, carbon monoxide and mixtures thereof.

11. A process as set forth in claim 10 wherein the non-oxidizing environment consists essentially of hydrogen.

12. A process as set forth in claim 4 wherein the non-oxidizing environment consists essentially of a non-oxidizing gas selected from the group consisting of nitrogen, argon, helium and mixtures thereof.

13. A process as set forth in claim 12 wherein the non-oxidizing environment consists essentially of nitrogen.

14. A process as set forth in claim 12 wherein the reaction product mixture is filtered to separate at least a portion of the oxidized reagent from the reaction product mixture, the product fraction comprising the filtrate produced.

15. A process as set forth in claim 14 wherein the catalyst slurry fraction is exposed to the non-oxidizing environment by introducing the non-oxidizing gas into a vessel containing the catalyst slurry fraction in a manner such that the non-oxidizing gas introduced into the vessel passes through the catalyst slurry fraction.

16. A process as set forth in claim 15 wherein the catalyst slurry fraction is agitated by a rotating impeller immersed in the catalyst slurry fraction as the non-oxidizing gas passes through the catalyst slurry fraction.

17. A process as set forth in claim 16 wherein the de-oxygenated catalyst slurry fraction has a dissolved oxygen concentration of no greater than about 5 ppm by weight.

18. A process as set forth in claim 17 wherein the de-oxygenated catalyst slurry fraction has a dissolved oxygen concentration of no greater than about 3 ppm by weight.

19. A process as set forth in claim 18 wherein the de-oxygenated catalyst slurry fraction has a dissolved oxygen concentration no greater than about 1 ppm by weight.

20. A process as set forth in claim 19 wherein the de-oxygenated catalyst slurry fraction has a dissolved oxygen concentration no greater than about 0.5 ppm by weight.

21. A process for the preparation of an N-(phosphonomethyl)glycine product, the process comprising:

contacting an aqueous reaction mixture comprising an N-(phosphonomethyl)iminodiacetic acid substrate and a heterogenous oxidation catalyst with an oxygen-containing gas in an oxidation reaction zone to oxidize the N-(phosphonomethyl)iminodiacetic acid substrate and produce an aqueous reaction product mixture comprising the N-(phosphonomethyl)glycine product and the oxidation catalyst, the oxidation catalyst comprising a noble metal deposited on a carbon support;

filtering the reaction product mixture to separate at least a portion of the N-(phosphonomethyl)glycine product from the reaction product mixture and form a filtrate product fraction comprising the separated N-(phosphonomethyl)glycine product substantially free of the oxidation catalyst and a catalyst slurry fraction comprising the oxidation catalyst in contact with a liquid medium;

subjecting the catalyst slurry fraction to a de-oxygenation treatment, the de-oxygenation treatment comprising exposing the catalyst slurry fraction to a non-oxidizing environment comprising a non-oxidizing gas by introducing the non-oxidizing gas into a vessel containing the catalyst slurry fraction in a manner such that the non-oxidizing gas introduced into the vessel passes through the catalyst slurry fraction; and recycling and introducing the de-oxygenated catalyst slurry fraction into the oxidation reaction zone.

22. A process as set forth in claim 21 wherein the non-oxidizing environment consists essentially of nitrogen.

23. A process as set forth in claim 21 wherein the catalyst slurry fraction is agitated by a rotating impeller immersed in the catalyst slurry fraction as the non-oxidizing gas passes through the catalyst slurry fraction.

24. A process as set forth in claim 21 wherein the de-oxygenated catalyst slurry fraction has a dissolved oxygen concentration of no greater than about 5 ppm by weight.

25. A process as set forth in claim 24 wherein the de-oxygenated catalyst slurry fraction has a dissolved oxygen concentration of no greater than about 3 ppm by weight.

26. A process as set forth in claim 25 wherein the de-oxygenated catalyst slurry fraction has a dissolved oxygen concentration no greater than about 1 ppm by weight.

27. A process as set forth in claim 26 wherein the de-oxygenated catalyst slurry fraction has a dissolved oxygen concentration no greater than about 0.5 ppm by weight.

28. A process for oxidizing a reagent, the process comprising:

contacting an aqueous reaction mixture comprising the reagent and a heterogenous oxidation catalyst with an oxygen-containing gas in an oxidation reaction zone to oxidize the reagent and produce an aqueous reaction product mixture comprising the oxidized reagent and the oxidation catalyst, the oxidation catalyst comprising a noble metal deposited on a carbon support;

subjecting a catalyst slurry comprising the oxidation catalyst in contact with a liquid medium to a de-oxygenation treatment, the de-oxygenation treatment comprising exposing the catalyst slurry to a non-oxidizing environment comprising a reducing gas; and recycling and introducing oxidation catalyst obtained in the de-oxygenated catalyst slurry into the oxidation reaction zone.

29. A process as set forth in claim 28 wherein the reagent is selected from the group consisting of N-(phosphonomethyl)iminodiacetic acid substrates, N-substituted-N-(phosphonomethyl)glycine substrates, formaldehyde, formic acid and mixtures thereof.

30. A process as set forth in claim 29 wherein the reagent is an N-(phosphonomethyl)iminodiacetic acid substrate and the reaction product mixture comprises an N-(phosphonomethyl)glycine product.

31. A process as set forth in claim 28 wherein the non-oxidizing environment consists essentially of a reducing gas.

32. A process as set forth in claim 31 wherein the reducing gas is selected from the group consisting of hydrogen, carbon monoxide and mixtures thereof.

33. A process as set forth in claim 31 wherein the non-oxidizing environment consists essentially of hydrogen.

34. A process as set forth in claim 28 wherein the catalyst slurry subjected to the de-oxygenation treatment comprises the aqueous reaction product mixture.

35. A process as set forth in claim 28 further comprising separating at least a portion of the oxidized reagent from the aqueous reaction product mixture to form the catalyst slurry and a product fraction comprising the separated oxidized reagent substantially free of the oxidation catalyst.

36. A process as set forth in claim 35 wherein the aqueous reaction product mixture is filtered to separate at least a portion of the oxidized reagent from the reaction product mixture, the product fraction comprising the filtrate produced.

37. A process as set forth in claim 36 wherein the catalyst slurry is exposed to the non-oxidizing environment by introducing the reducing gas into a vessel containing the catalyst slurry in a manner such that the reducing gas introduced into the vessel passes through the catalyst slurry.

38. A process as set forth in claim 37 wherein the catalyst slurry is agitated by a rotating impeller immersed in the catalyst slurry as the reducing gas passes through the catalyst slurry.

39. A process as set forth in claim 38 wherein the de-oxygenated catalyst slurry has a dissolved oxygen concentration of no greater than about 5 ppm by weight.

40. A process as set forth in claim 39 wherein the de-oxygenated catalyst slurry has a dissolved oxygen concentration of no greater than about 3 ppm by weight.

41. A process as set forth in claim 40 wherein the de-oxygenated catalyst slurry has a dissolved oxygen concentration no greater than about 1 ppm by weight.

42. A process as set forth in claim 41 wherein the de-oxygenated catalyst slurry has a dissolved oxygen concentration no greater than about 0.5 ppm by weight.

43. A process for the preparation of an N-(phosphonomethyl)glycine product, the process comprising:

contacting an aqueous reaction mixture comprising an N-(phosphonomethyl)iminodiacetic acid substrate and a heterogenous oxidation catalyst with an oxygen-containing gas in an oxidation reaction zone to oxidize the N-(phosphonomethyl)iminodiacetic acid substrate and produce an aqueous reaction product mixture comprising the N-(phosphonomethyl)glycine product and the oxidation catalyst, the oxidation catalyst comprising a noble metal deposited on a carbon support;

filtering the reaction product mixture to separate at least a portion of the N-(phosphonomethyl)glycine product from the reaction product mixture and form a filtrate product fraction comprising the separated N-(phosphonomethyl)glycine product substantially free of the oxidation catalyst and a catalyst slurry fraction comprising the oxidation catalyst in contact with a liquid medium;

subjecting the catalyst slurry fraction to a de-oxygenation treatment, the de-oxygenation treatment comprising exposing the catalyst slurry fraction to a non-oxidizing environment comprising a reducing gas by introducing the reducing gas into a vessel containing the catalyst slurry fraction in a manner such that the reducing gas introduced into the vessel passes through the catalyst slurry fraction; and recycling and introducing the de-oxygenated catalyst slurry fraction into the oxidation reaction zone.

44. A process as set forth in claim 43 wherein the non-oxidizing environment consists essentially of a reducing gas.

45. A process as set forth in claim 44 wherein the reducing gas is selected from the group consisting of hydrogen, carbon monoxide and mixtures thereof.

46. A process as set forth in claim 45 wherein the non-oxidizing environment consists essentially of hydrogen.

47. A process as set forth in claim 43 wherein the catalyst slurry fraction is agitated by a rotating impeller immersed in the catalyst slurry fraction as the reducing gas passes through the catalyst slurry fraction.

48. A process as set forth in claim 43 wherein the de-oxygenated catalyst slurry fraction has a dissolved oxygen concentration of no greater than about 5 ppm by weight.

49. A process as set forth in claim 48 wherein the de-oxygenated catalyst slurry fraction has a dissolved oxygen concentration of no greater than about 3 ppm by weight.

50. A process as set forth in claim 49 wherein the de-oxygenated catalyst slurry fraction has a dissolved oxygen concentration no greater than about 1 ppm by weight.

51. A process as set forth in claim 50 wherein the de-oxygenated catalyst slurry fraction has a dissolved oxygen concentration no greater than about 0.5 ppm by weight.

* * * * *